(12) United States Patent
Aljuri et al.

(10) Patent No.: US 11,337,719 B2
(45) Date of Patent: May 24, 2022

(54) WATER ENUCLEATION OF THE PROSTATE

(71) Applicant: PROCEPT BIOROBOTICS CORPORATION, Redwood City, CA (US)

(72) Inventors: Nikolai Aljuri, Hillsborough, CA (US); Surag Mantri, Sunnyvale, CA (US)

(73) Assignee: PROCEPT BIOROBOTICS CORPORATION, Redwood City, CA (US)

( * ) Notice: Subject to any disclaimer, the term of this patent is extended or adjusted under 35 U.S.C. 154(b) by 0 days.

(21) Appl. No.: 16/121,489

(22) Filed: Sep. 4, 2018

(65) Prior Publication Data
US 2019/0053820 A1    Feb. 21, 2019

Related U.S. Application Data

(63) Continuation of application No. 14/244,452, filed on Apr. 3, 2014, now Pat. No. 10,098,656.
(Continued)

(51) Int. Cl.
*A61B 17/32* (2006.01)
*A61B 17/3203* (2006.01)
(Continued)

(52) U.S. Cl.
CPC .......... *A61B 17/3203* (2013.01); *A61B 90/30* (2016.02); *A61B 2017/00274* (2013.01); *A61B 2018/00547* (2013.01); *A61B 2018/206* (2013.01)

(58) Field of Classification Search
CPC .......... A61B 17/3203; A61B 17/32037; A61B 2018/00547; A61B 2017/32032; A61B 2017/32035; A61B 2017/00274
See application file for complete search history.

(56) References Cited

U.S. PATENT DOCUMENTS 5,176,677 A   1/1993   Wuchinioh
5,520,636 A   5/1996   Korth
(Continued)

FOREIGN PATENT DOCUMENTS

CN   1276737    12/2000
CN   1937965    3/2007
(Continued)

OTHER PUBLICATIONS

Desai, et al. Single-Port Transvesical Simple Prostatectomy: Initial Clinical Report. Urology. 2008; 72(5):960-965.
(Continued)

*Primary Examiner* — Tuan V Nguyen
(74) *Attorney, Agent, or Firm* — FisherBroyles LLP; John Shimmick

(57) ABSTRACT

Embodiments of the present invention provide improved methods and apparatus of treating the prostate. In many embodiments, at least a portion of the prostate is enucleated with a water jet, in order to decrease the invasiveness of the surgery. The access to the prostate can be provided with one or more of open surgical access, percutaneous access, or urethral access. The prostate can be enucleated such that an inner portion of the prostate comprising adenomatous tissue of the prostate is separated from a portion an outer the prostate comprising the capsule. In many embodiments, the patient is treated with energy of the water jet configured to separate the capsule from the inner tissue of the prostate and to inhibit cutting of blood vessels.

10 Claims, 27 Drawing Sheets

Related U.S. Application Data

(60) Provisional application No. 61/808,197, filed on Apr. 3, 2013.

(51) Int. Cl.
*A61B 18/20* (2006.01)
*A61B 17/00* (2006.01)
*A61B 18/00* (2006.01)
*A61B 90/30* (2016.01)

(56) References Cited

U.S. PATENT DOCUMENTS

| | | | |
|---|---|---|---|
| 5,782,848 | A | 7/1998 | Lennox |
| 5,788,667 | A | 8/1998 | Stoller |
| 7,882,841 | B2 | 2/2011 | Aljuri |
| 9,622,768 | B2 * | 4/2017 | Fischer .............. A61B 17/3203 |
| 9,867,635 | B2 | 1/2018 | Alvarez |
| 2001/0047147 | A1 | 11/2001 | Slepian |
| 2002/0111579 | A1 * | 8/2002 | Moutafis ............ A61B 17/3203 604/43 |
| 2009/0018490 | A1 * | 1/2009 | Wuchinich ..... A61B 17/320068 604/22 |
| 2009/0018533 | A1 | 1/2009 | Perkins |
| 2009/0227998 | A1 | 9/2009 | Aljuri |
| 2009/0254075 | A1 | 10/2009 | Paz |
| 2010/0036471 | A1 | 2/2010 | Dolan |
| 2010/0179528 | A1 | 7/2010 | Shadduck |
| 2011/0184391 | A1 | 7/2011 | Aljuri |
| 2013/0116716 | A1 * | 5/2013 | Bahls ................ A61B 17/3203 606/167 |
| 2014/0012077 | A1 | 1/2014 | Fagnani |
| 2014/0309649 | A1 | 10/2014 | Alvarez |
| 2015/0025539 | A1 | 1/2015 | Alvarez |

FOREIGN PATENT DOCUMENTS

| | | |
|---|---|---|
| CN | 102271595 | 12/2011 |
| CN | 102762168 | 10/2012 |
| CN | 102905633 | 1/2013 |
| CN | 104203078 | 12/2014 |
| EP | 0904030 | 3/1999 |
| JP | S63105755 | 5/1988 |
| KR | 20060128572 | 12/2006 |
| WO | 03005889 | 1/2003 |
| WO | 2007013076 | 2/2007 |
| WO | 2008083407 | 7/2008 |
| WO | 2009111736 | 9/2009 |
| WO | 2011097505 | 8/2011 |
| WO | 2013130895 | 9/2013 |
| WO | 2013130895 A1 | 9/2013 |
| WO | 2014127242 | 8/2014 |

OTHER PUBLICATIONS

European Search Report dated Oct. 17, 2016 for European application No. 14780121.1.

International search report and written opinion dated Aug. 14, 2014 for PCT/US2014/032879.

Krambeck. Evolution and success of holmium laser enucleation of the prostate. Indian J Urol. Jul. 2010;26(3):404-9. doi: 10.4103/0970-1591.70582.

Ramsay L Kuo, Holmium Laser Enucleation of the Prostate: A Technical Update, Jun, 6, 2003, World Journal of Surgical Oncology, I:6.

U.S. Appl. No. 61/808,197, filed Apr. 3, 2013, Aljuri et al.

* cited by examiner

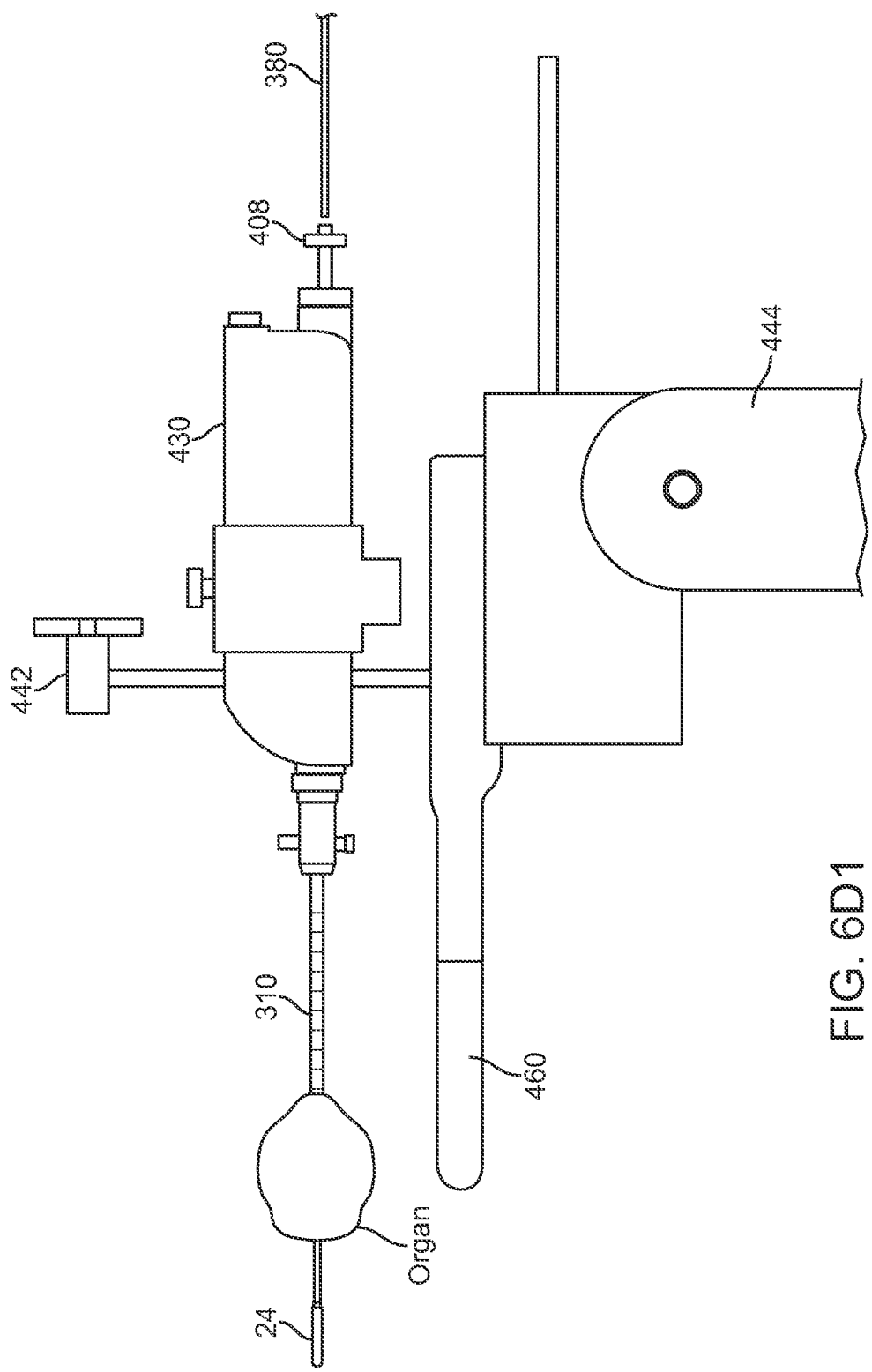

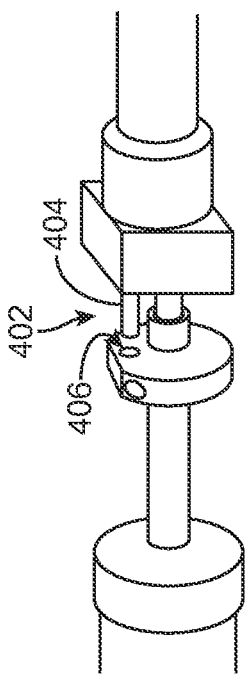
FIG. 6D3
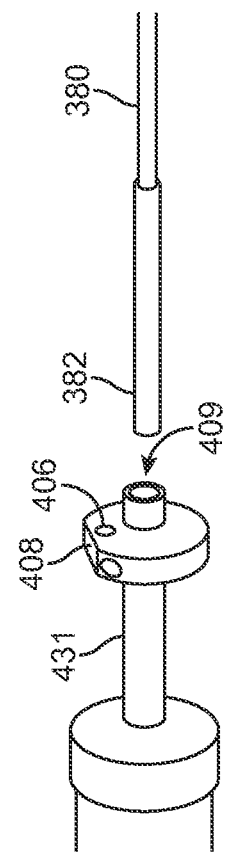
FIG. 6D2
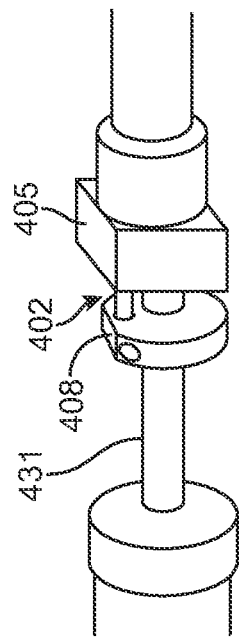
FIG. 6D4

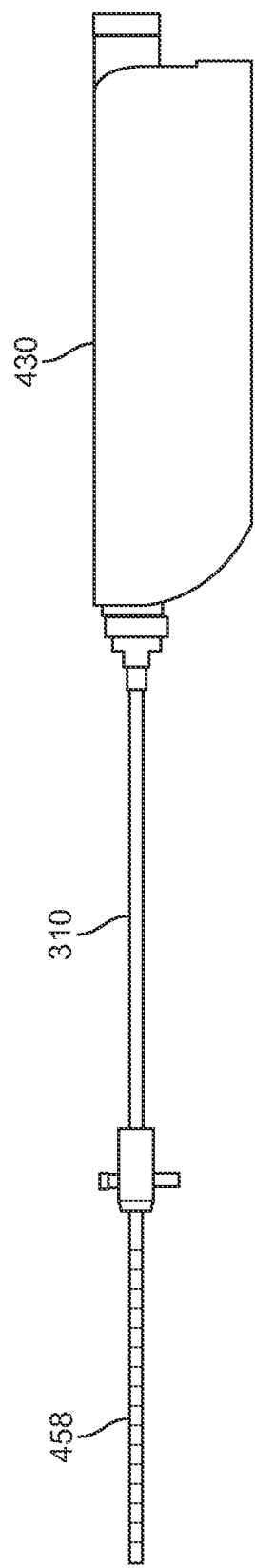

WATER ENUCLEATION OF THE PROSTATE

CROSS-REFERENCE

The present application is a continuation of U.S. patent application Ser. No. 14/244,452, filed Apr. 3, 2014, now U.S. Pat. No. 10,098,656, issued Oct. 16, 2018, which claims the benefit of U.S. Provisional Application No. 61/808,197, filed Apr. 3, 2013, which applications are incorporated herein by reference.

INCORPORATION BY REFERENCE

The subject matter of the present application is related to and incorporates by reference the complete disclosures of the following U.S. Patents and pending applications: U.S. patent application Ser. No. 12/399,585, filed Mar. 6, 2009, entitled "TISSUE ABLATION AND CAUTERY WITH OPTICAL ENERGY CARRIED IN FLUID STREAM", now U.S. Pat. No. 8,814,921; U.S. patent application Ser. No. 12/700,568, filed Feb. 4, 2010, entitled "MULTI FLUID TISSUE RESECTION METHODS AND DEVICES", now U.S. Pat. Nos. 9,232,959; and 7,882,841, which issued 8 Feb. 2011 and which is entitled "MINIMALLY INVASIVE METHODS AND DEVICES FOR THE TREATMENT OF PROSTATE DISEASES"; and International Application No. PCT/US2013/028441, which was filed Feb. 28, 2013, entitled "AUTOMATED IMAGE-GUIDED TISSUE RESECTION AND TREATMENT".

BACKGROUND

The field of the present invention is related to the treatment tissue, and more specifically to the treatment of an organ such as the prostate with fluid stream energy.

Prior methods and apparatus of treating disorders related to tissue can be less than ideal in at least some instances. For example, the prostate can swell with age, and may require removal. In some instances, the prostate may comprise cancerous tissue requiring removal. In either case, surgical removal of the prostate can be more invasive and can require a longer recovery time than would be ideal.

Surgical enucleation of the prostate has been proposed and performed to remove the prostate. Surgical enucleation of the prostate offers the potential to remove enlarged prostate tissue, such as an adenoma of the prostate. However, surgical enucleation of the prostate can be more invasive than would be ideal, and may rely on an open incision. Percutaneous access of the prostate can provide enucleation and effective removal of enlarged prostate tissue and can be provided with access through the skin of patient and bladder in order to access the prostate. However, recovery time of percutaneous enucleation of the prostate can be longer than would be ideal. Recently, Holmium laser enucleation of the prostate (hereinafter "HOLEP") has been proposed. Transurethral enucleation of the prostate has the advantage of decreased invasiveness as the prostate can be accessed through the urethra. However, transurethral enucleation is a complicated and delicate procedure that may require considerable surgical skill, and is not readily available to many patients, possible due to the complexity of the procedure and surgical skill required. Furthermore, HOLEP has the disadvantage of patient bleeding and recovery times that can be less than ideal in at least some instances.

In light of the above, it would be helpful to provide improved methods and apparatus for treating the prostate. Ideally, such methods and apparatus would be less invasive, provide improved outcomes, and be readily practiced by many surgeons such that many patients would be able receive the benefits. At least some of these objectives will be met by the inventions described hereinafter.

SUMMARY

Embodiments of the present invention provide improved methods and apparatus of treating the prostate. In many embodiments at least a portion of the prostate is enucleated with a water jet, in order to decrease the invasiveness of the surgery. The access to the prostate can be provided with one or more of open surgical access, percutaneous access, or urethral access. The prostate can be enucleated such that an inner portion of the prostate comprising adenomatous tissue of the prostate is separated from a portion an outer the prostate comprising the capsule. In many embodiments the patient is treated with energy of the water jet configured to separate the capsule from the inner tissue of the prostate and to inhibit cutting of collagen-rich tissue such as blood vessels and the capsule of the prostate. In many embodiments, the urethral wall is resected with the water jet at a first luminal location near the neck of the bladder and at a second luminal location near the verumontanum of the urethra, in which the second luminal location is toward the bladder neck from the verumontanum. The prostate comprises three lobes: two lateral lobes and one medial lobe. While the lobes can be enucleated in many ways, in many embodiments at least a portion of each of the three lobes is enucleated separately with the water jet in order to decrease the invasiveness of the surgery. Alternatively or in combination, two or more lobes can be enucleated together, such as with open surgical access.

The energy of the water jet may be adjusted in one or more of many ways to provide enucleation of the prostate with decreased cutting of blood vessels, in order to decrease the invasiveness of the procedure. In many embodiments, the jet is adjusted to a first amount of energy to resect the urethra and a second amount of energy to separate the inner prostate tissue from the capsule with enucleation. In many embodiments, an entrainment region of the jet can be imaged, for example optically or with ultrasound, and the visible region of the jet adjusted to configure the water jet for one or more of resection of the urethra or for separation of the capsule from the inner prostate tissue.

In many embodiments, the visible region of the jet comprises an entrainment region of cavitations that increase scatter of imaging energy transmitted through the jet, for example light energy or ultrasound imaging energy, such that the jet appears in the image as a cold flame when configured to resect tissue. In many embodiments, the visible region of the jet comprising the entrainment region extending from the orifice to the visible flame tip is adjusted to a length within a range from about 2 to 5 mm under user visualization, and the probe can be used to resect the urethra. The separation of the capsule from the inner layer of the prostate can be provided with the length of the visible jet within the range from 1 to 5 mm, for example from 1 to 3 mm.

The visible region comprising the entrainment region of the jet can be adjusted with one or more of a pressure, a flow rate of liquid through the probe, or an opening of the orifice of the probe. In many embodiments, the probe is selected to based on the orifice of the probe in order provide a desired "flame" length from the orifice to the tip of the "flame" comprising the entrainment region. In many embodiments, the fluid stream comprises a divergent fluid stream such that cutting of collagenous tissue such as the urethra and blood vessels at a distance beyond the tip of the flame is inhibited.

Work in relation to embodiments suggests that enucleation can be provided with fluid flow at distances beyond the tip of the entrainment region of cavitation comprising the "flame", such that enucleation can be provided by separating the capsule from the inner prostate tissue at distances beyond the tip of the "flame". Consequently, the cutting of blood vessels can be further inhibited during separation of the capsule from the inner prostate tissue with appropriate adjustment of the water jet for separating the capsule from the inner layers of the prostate. In many alternative or combinational embodiments, the distance from the orifice to the tip of the entrainment region comprising the cold flame can be decreased subsequent to cutting the urethra to further inhibit cutting of vascular tissue during separation of the capsule from the inner prostate tissue. Alternatively or in combination, a first probe having a first orifice can be selected and advanced into the urethra for cutting the urethra and second probe having a second orifice can be used to separate the inner prostate from the capsule.

In many embodiments, urethral access to the prostate is provided through a natural opening of the urethra to the exterior of the patient. This urethral access has the advantage of decreasing invasiveness of the surgery. A plurality of instruments can be introduced into the urethra, for example an endoscope to visualize the treatment area, an elongate treatment probe comprising an opening for the water jet, and a morcellating probe to morcellate separately at least a portion of each lobe of the prostate from within the bladder. The water jet can be used to resect the urethra near the bladder neck and near the verumontanum under endoscopic visualization. At least a portion of each lobe of the prostate can be separately enucleated and advanced into the bladder. Each enucleated lobe of the prostate can be morcellated from within the bladder.

The water jet can be combined with one or more of many additional surgical configurations such as insufflation of the urethra, morcellation of each of the enucleated lobes of the prostate, and laser energy delivery through the water jet orifice for one or more of cautery, laser cutting, or laser illumination of the rejection resected with the jet. Alternatively or in combination, a bag may be placed over the water jet such that the water jet comprises a water hammer to strike the tissue for separation with the portion of the bag impinged upon by the water jet.

Aspects of the present disclosure provide a method of at least partially enucleating a prostate. A probe may be advanced at least partially into the patient. A urethra of the patient may be resected at a first location and a second location with a water jet. An inner tissue of the prostate may be separated from a capsule of the prostate with the water jet.

The probe may be advanced into the patient with one or more of open surgical access, percutaneous access, or urethral access. The first location where the urethra may be resected may be situated near a bladder neck of the urethra and the second location may be situated near a verumontanum and toward the bladder neck from the verumontanum. The resection of the urethra may comprise a plurality of resections extending between the first location and the second location and the plurality of resections may extend from the urethra to the capsule.

An energy of the water jet may be adjusted to separate the capsule from the inner tissue and inhibit resection of the capsule and blood vessels. The water jet may comprise a divergent stream. An energy of the water jet may adjusted based on an image of an entrainment region of the water jet when the probe has been inserted at least partially into the urethra. The water jet may be adjusted to a first amount of energy to resect the urethra at the first location and the second location and a second amount of energy to separate the outer capsule of the prostate from the inner tissue.

A first orifice of a first probe may be used to provide the jet to resect the urethra and a second orifice of a second probe may be used to provide the jet to separate the capsule from the inner prostate tissue.

The probe may be advanced into a natural opening of the urethra to access the urethra. The urethra may be resected at the first location and the second location with first probe with the jet extending to a side of the first probe to resect the urethra. The capsule may be separated from the inner layer with a second probe having the jet extending from the end of the probe at a different angle than the first probe.

Aspects of the present disclosure provide an apparatus to at least partially enucleate a prostate of a patient. The apparatus may comprise a probe to advance at least partially into the patient. The probe may be configured to provide a water jet to reset a urethra of the patient at a first location and a second location and to separate an inner tissue of the prostate from a capsule of the prostate.

The probe may be configured to advance into the patient with one or more of open surgical access, percutaneous access or urethral access. The probe may be configured to provide the water jet to the first location situated near a bladder neck of the urethra and the second location situated near a verumontanum and toward the bladder neck from the verumontanum. The probe may be configured to resect the urethra with a plurality of resections extending between the first location and the second location. The plurality of resections may extend from the urethra to the capsule.

The energy of the water jet may be adjustable to separate the capsule from the inner tissue and inhibit resection of the capsule and blood vessels. The water jet may comprise a divergent stream. The energy of the water jet may be adjustable based on an image of an entrainment region of the water jet when the probe has been inserted at least partially into the urethra. The water jet may be adjustable to a first amount of energy to resect the urethra at the first location and the second location and a second amount of energy to separate the outer capsule of the prostate from the inner tissue.

A first orifice of a first probe may be configured to provide the jet to resect the urethra and a second orifice of a second probe may be configured to provide the jet to separate the capsule from the inner prostate tissue. The probe may be configured to advance into a natural opening of the urethra to access the urethra. The probe may be configured to resect the urethra at the first location and the second location with first probe with the jet extending to a side of the first probe to resect the urethra. The second probe may be configured to separate the capsule from the inner layer with a second probe having the jet extending from the end of the probe at a different angle than the first probe.

BRIEF DESCRIPTION OF THE DRAWINGS

A better understanding of the features and advantages of the present disclosure will be obtained by reference to the following detailed description that sets forth illustrative embodiments, in which the principles of the disclosure are utilized, and the accompanying drawings of which:

FIG. 6D1 shows rapid exchange of a carrier when the linkage is coupled to the elongate element anchored to a target location of an organ, in accordance with embodiments;

FIG. 6D2 shows alignment of the distal tip of the carrier with the proximal end of the linkage to insert the carrier tube as in FIG. 6D1;

FIG. 6D3 shows the carrier advanced toward a locking structure on the proximal end of the linkage as in FIG. 6D1;

FIG. 6D4 shows the carrier locked to the linkage as in FIGS. 6D1 and 6D2;

FIG. 6F shows advancement of an elongate element into a sheath;

DETAILED DESCRIPTION

A better understanding of the features and advantages of the present disclosure will be obtained by reference to the following detailed description that sets forth illustrative embodiments, in which the principles of embodiments of the invention are utilized, and the accompanying drawings.

Although the detailed description contains many specifics, these should not be construed as limiting the scope of the disclosure but merely as illustrating different examples and aspects of the present disclosure. It should be appreciated that the scope of the disclosure includes other embodiments not discussed in detail above. Various other modifications, changes and variations which will be apparent to those skilled in the art may be made in the arrangement, operation and details of the method and apparatus of the present disclosure provided herein without departing from the spirit and scope of the invention as described herein.

The embodiments disclosed herein can be combined in one or more of many ways to provide improved therapy to a patient. The disclosed embodiments can be combined with prior methods and apparatus to provide improved treatment, such as combination with known methods of prostate surgery and surgery of other tissues and organs, for example. It is to be understood that any one or more of the structures and steps as described herein can be combined with any one or more additional structures and steps of the methods and apparatus as described herein, the drawings and supporting text provide descriptions in accordance with embodiments.

As used herein like characters identify like elements.

Figure 1:
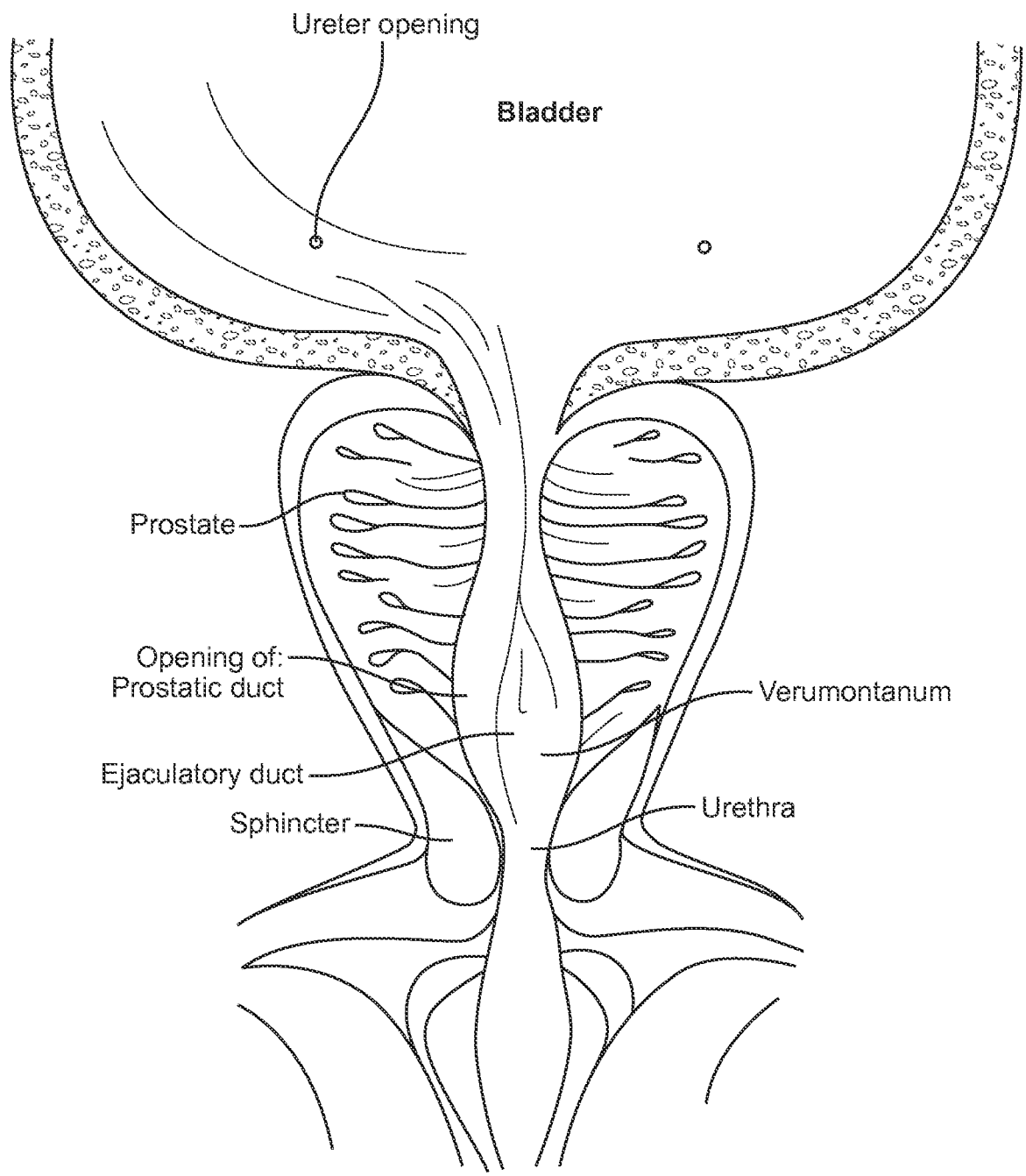
FIG. 1 shows anatomy of the patient having the prostate and verumontanum and bladder, suitable for incorporation in accordance with embodiments.

FIG. 1 shows anatomy of the patient having the Prostate, Verumontanum, and Bladder, suitable for incorporation in accordance with embodiments. FIG. 1A further shows the Ureter openings of the Bladder, the Openings of the Prostate duct, the Ejaculatory duct, and the Sphincter of the Bladder.

FIGS. 2A-2D show a method of percutaneous enucleation of the prostate with a water jet.

Figure 2A:
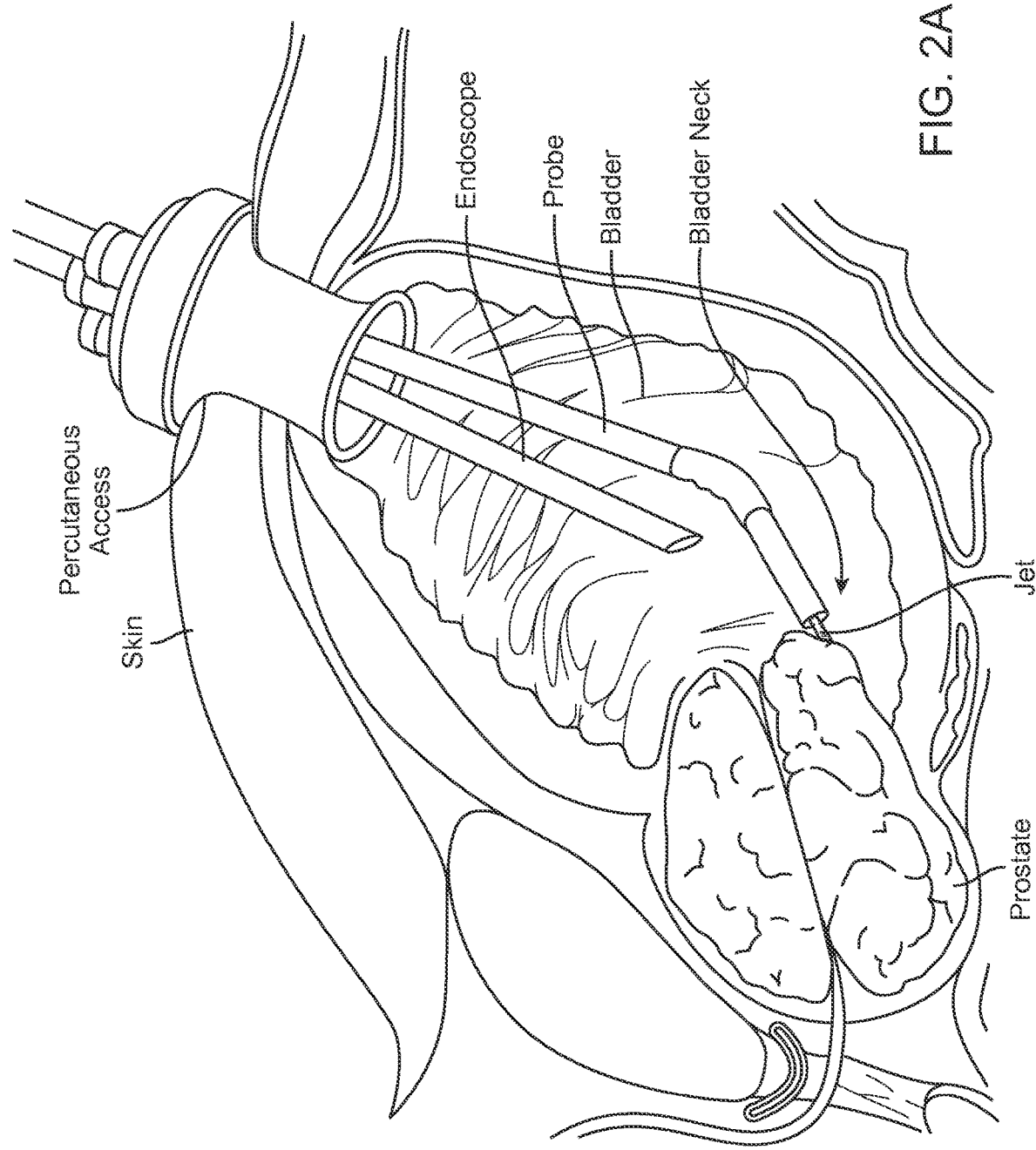
FIG. 2A shows transcutaneous resection of the prostate through the bladder, in accordance with embodiments.

FIG. 2A shows transcutaneous resection of the prostate through the bladder, in accordance with embodiments. An Endoscope and a Probe are advanced across the Skin into the Bladder through a Percutaneous Access. The distal end of the Probe is positioned near the Bladder Neck to direct a cutting Jet to the Prostate.

Figure 2B:
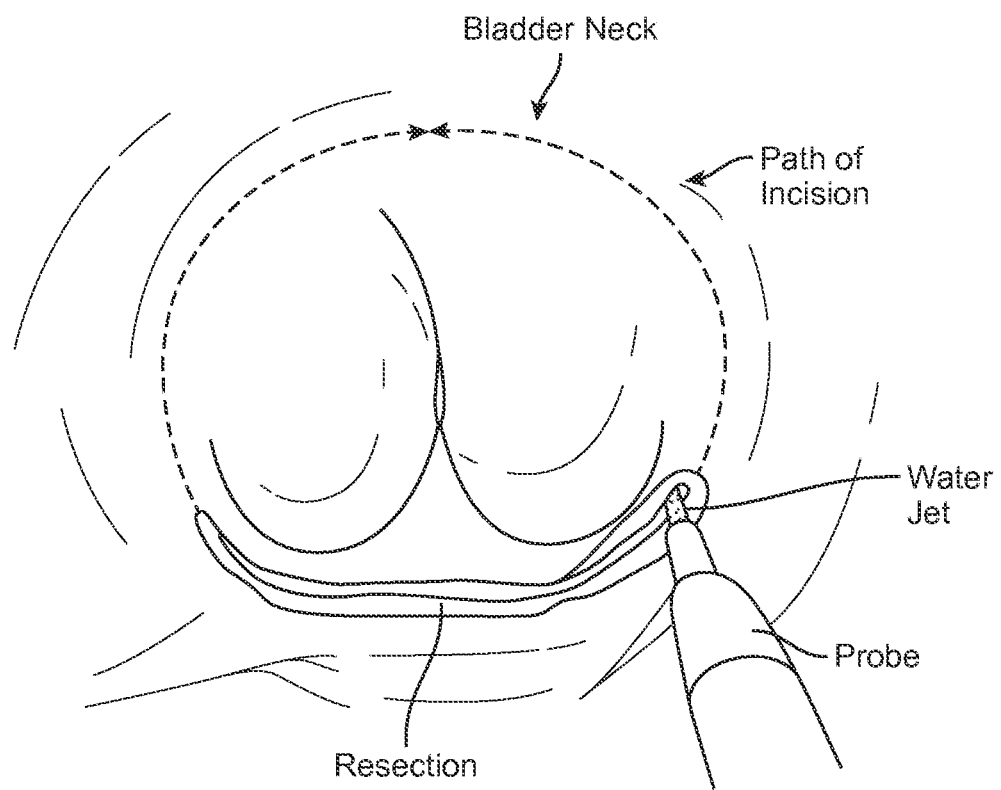
FIG. 2B shows resection of tissue near the bladder neck with the water jet and cutting of the urethra at a first location near the bladder neck, in accordance with embodiments.

FIG. 2B shows Resection of tissue near the Bladder Neck with the Water Jet and cutting of the urethra at a first location near the Bladder Neck, in accordance with embodiments. FIG. 2B further shows the Water Jet projected from the Probe along a Path of Incision.

Figure 2C:
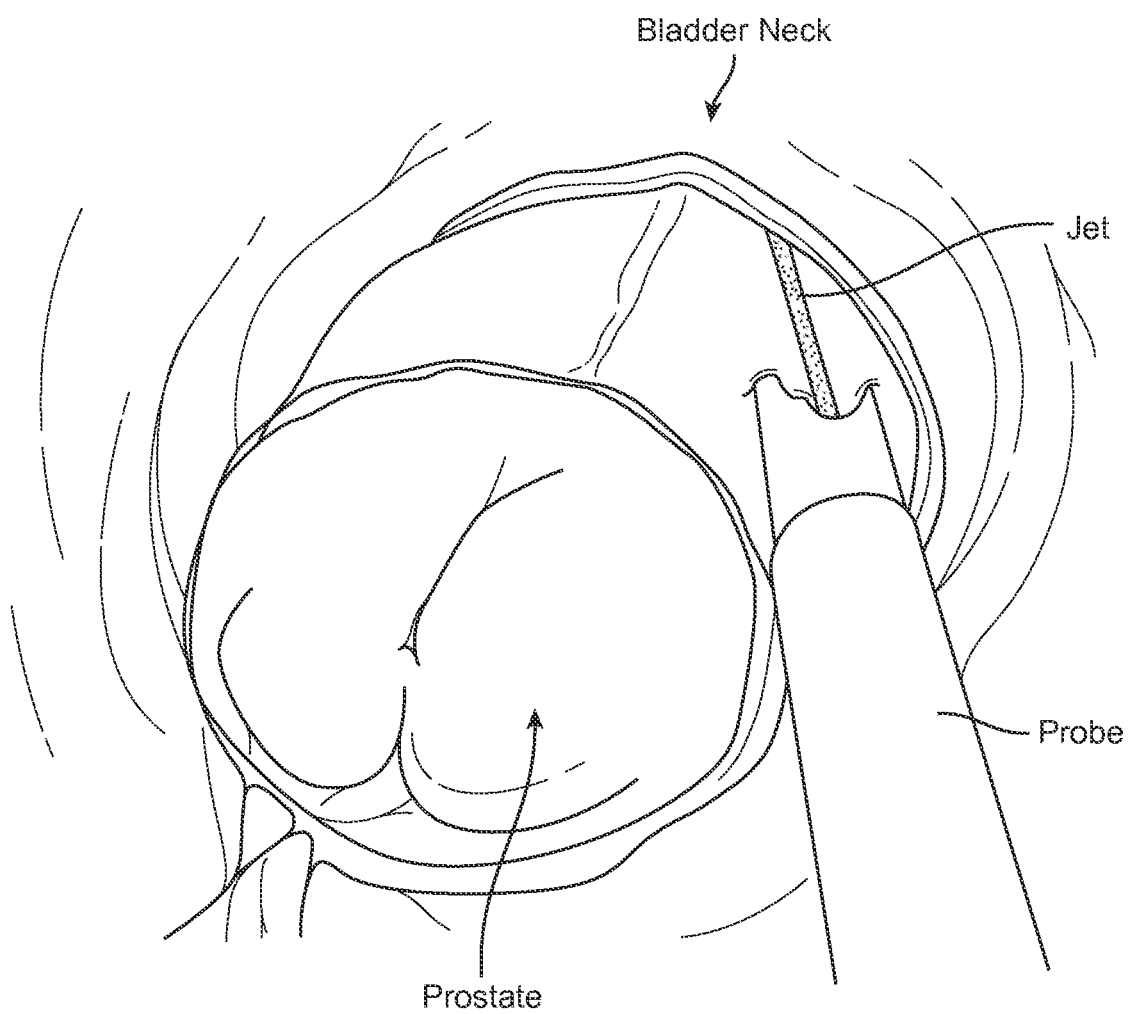
FIG. 2C shows enucleation of at least a portion of the prostate with the water jet to separate inner tissue of the prostate from the capsule, in accordance with embodiments.

FIG. 2C shows enucleation of at least a portion of the Prostate with the Water Jet to separate inner tissue of the Prostate from the capsule, in accordance with embodiments.

Figure 2D:
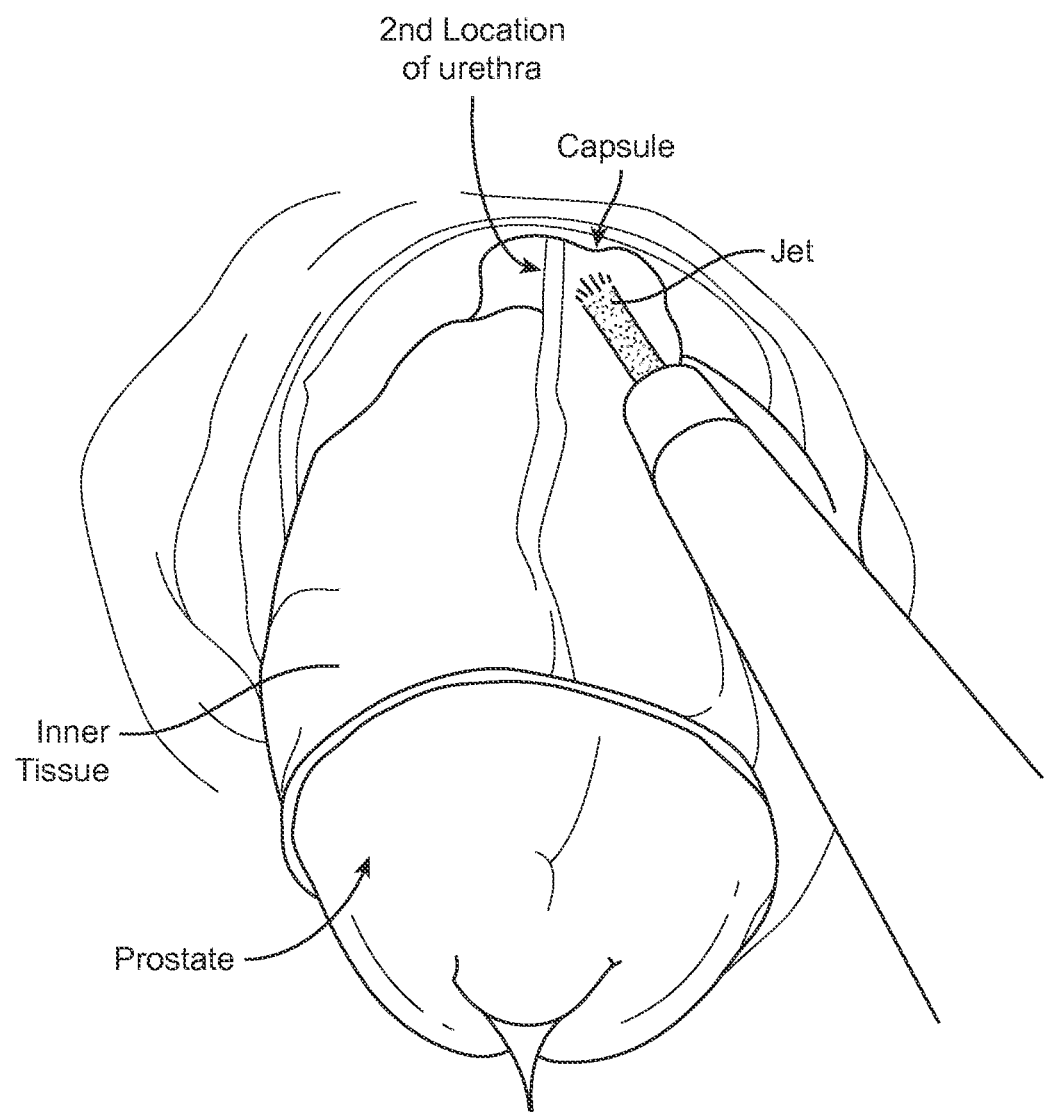
FIG. 2D shows a portion of the enucleated prostate advanced into bladder and separation of the capsule from the inner portion of the prostate near the second location of the urethra between the bladder neck and the verumontanum, in accordance with embodiments.

FIG. 2D shows a portion of the enucleated Prostate advanced into bladder and separation of the capsule from the inner portion (or Inner Tissue) of the Prostate near the second location ($2^{nd}$ location) of the Urethra between the Bladder Neck and the Verumontanum, in accordance with embodiments.

Figure 3A:
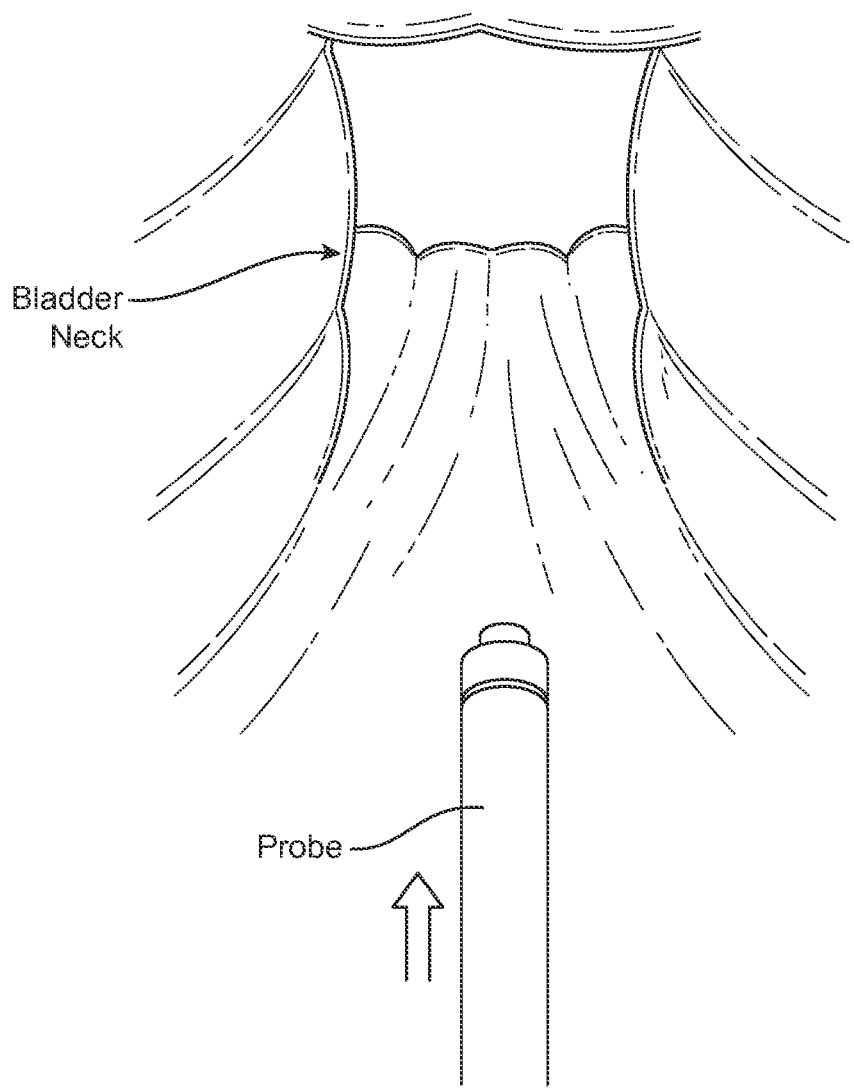
FIG. 3A shows a bladder neck and probe as seen through an endoscope with urethral access.
Figure 3B:
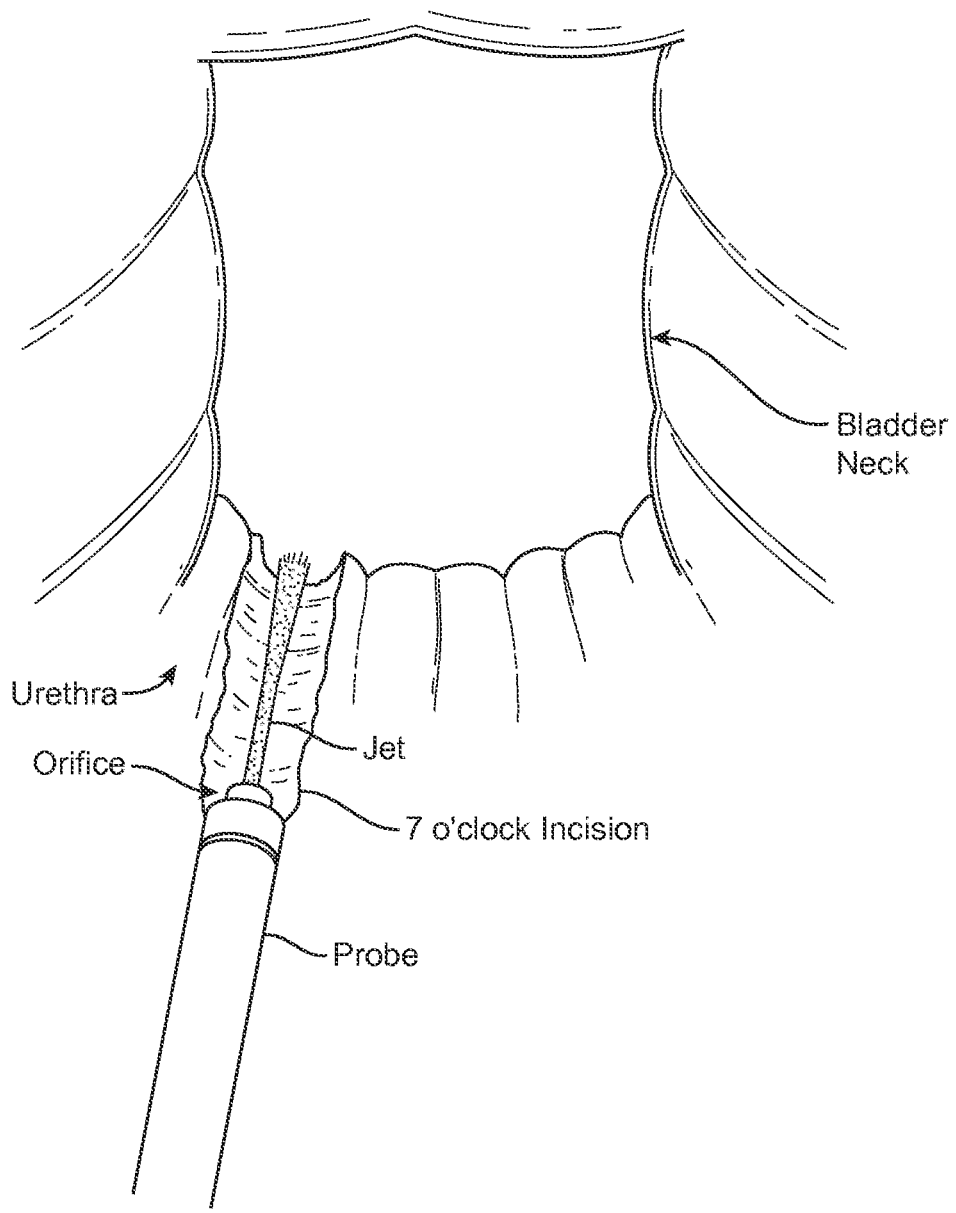
FIG. 3B shows a probe oriented for a 7 O'clock cut path along the urethra from the bladder neck to the verumontanum.
Figure 3C:
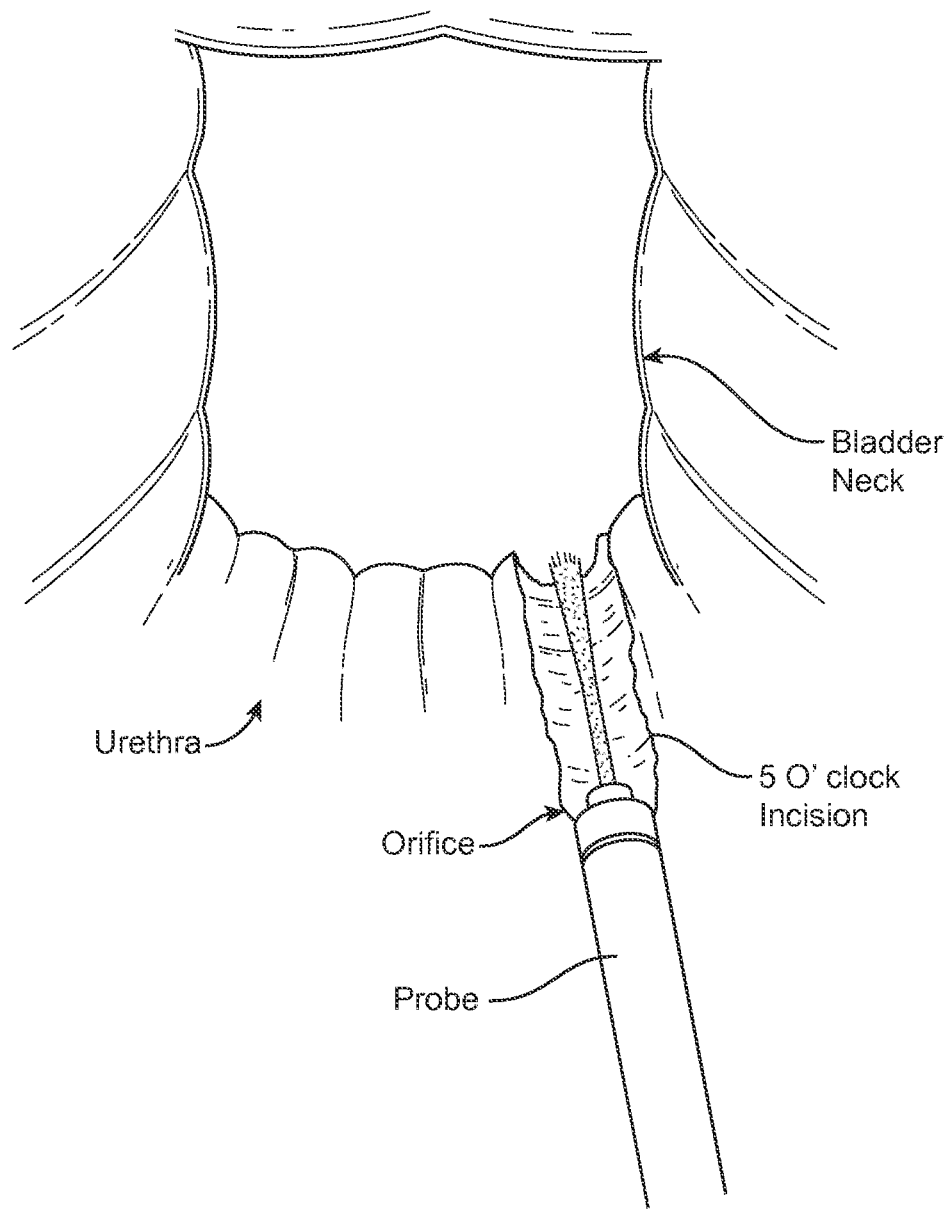
FIG. 3C shows a probe oriented for a 5 O'clock cut path along the urethra from the bladder neck to the verumontanum.

FIGS. 3A-3C show a method of transurethral enucleation of the prostate with a water jet.

FIG. 3A shows a Bladder Beck and Probe as seen through an endoscope with urethral access.

FIG. 3B shows the Probe oriented for a 7 O'clock incision or cut path along the Urethra from the Bladder Neck to the Verumontanum.

FIG. 3C shows the Probe oriented for a 5 O'clock incision or cut path along the Urethra from the Bladder neck to the Verumontanum.

Figure 4:
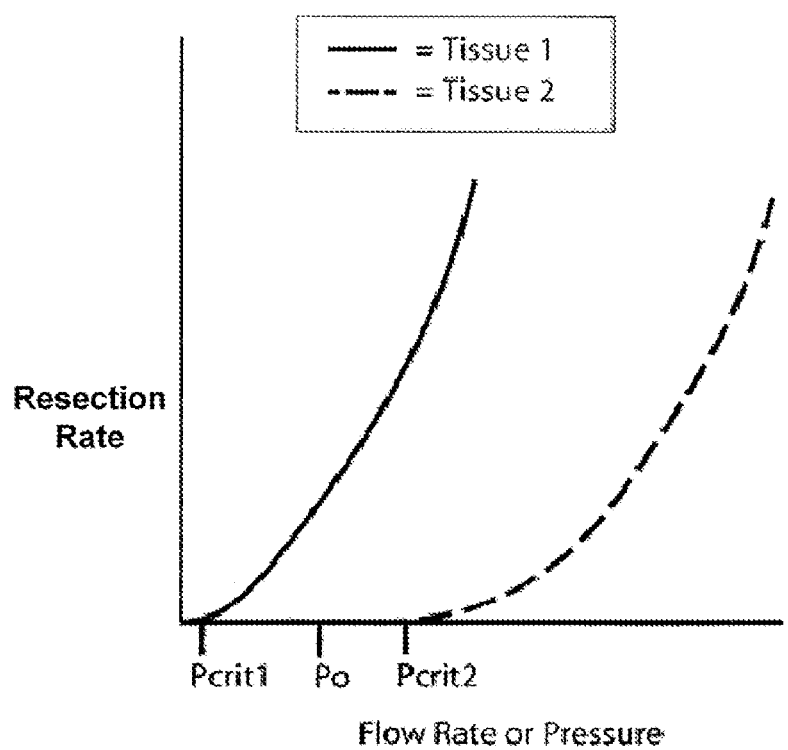
FIG. 4 is a graph of tissue resection rates demonstrating critical pressures.

An important aspect of resecting tissue in a multi-tissue environment according to the present embodiments is that it is possible to operate in a regime where one tissue type is resected and another tissue type remains substantially undamaged. This happens most strongly when operating at a pressure between the critical pressures of the two tissue types. As seen in FIG. 4, the operating pressure $p_0$ of the fluid stream may be configured to be greater than the critical pressure of tissue 1 ($p_0 > p_{crit1}$) so that tissue 1 experiences a resection rate that is greater than zero, while keeping the pressure p0 less than the critical pressure of tissue 2 ($p_0 < p_{crit2}$) so that tissue 2 experiences a rate of resection that is substantially near zero. In such a configuration, the fluid stream is said to be configured to selectively resect tissue 1 but not tissue 2.

In one embodiment configured to treat BPH, the fluid stream source pressure is configured to be above the critical pressure of glandular prostate tissue but below the critical pressure of non-glandular prostate tissue. In such an embodiment, the pressure is sufficiently high to resect glandular tissue, but too low to substantially resect or damage non-glandular tissue such as intra-prostate blood vessels, fibromuscular stroma, capsular tissue, etc. In one embodiment, the fluid is pressurized to a pressure within the range of about 1-30,000 psi before leaving the fluid delivery element, more preferably to a pressure within the range of about 50-1,500 psi, and most preferably to a pressure within the range of about 100-1,000 psi.

Figure 5:
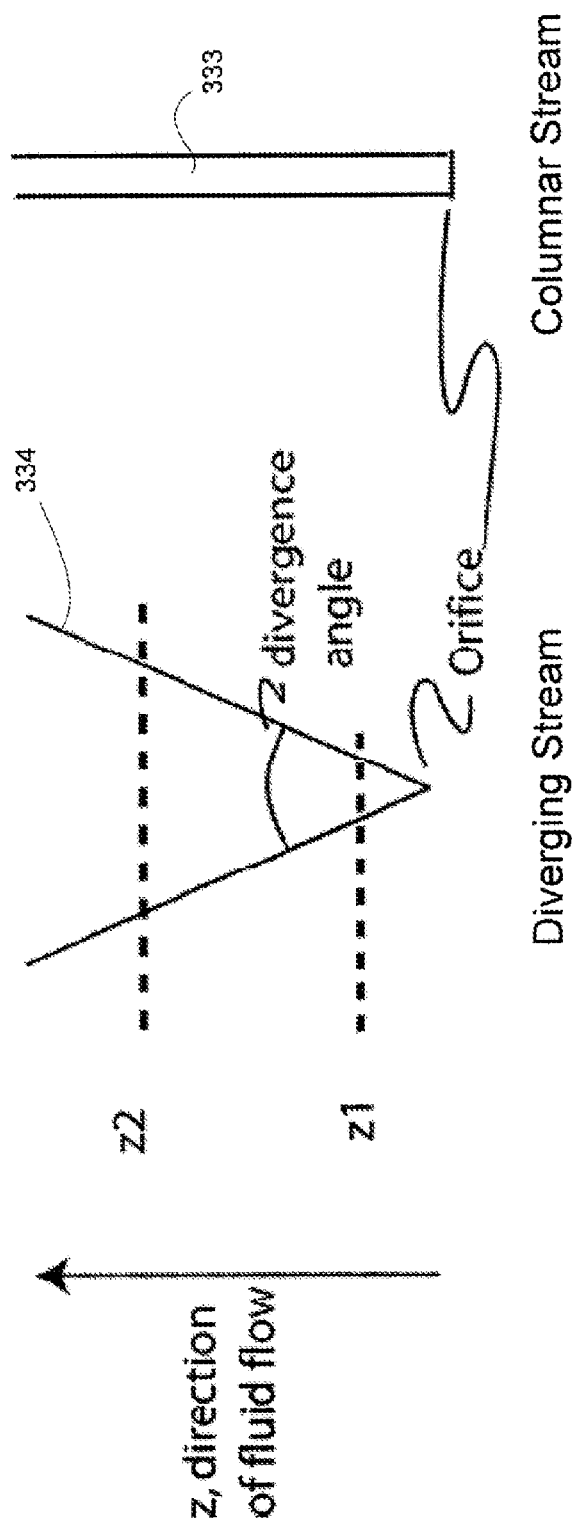
FIG. 5 illustrates a columnar fluid stream and a diverging fluid stream.

In addition, it is contemplated that the shape of the fluid stream also affects selective resection. While the fluid stream is exemplarily shown in FIG. 5 as a columnar fluid stream 333 or diverging fluid stream 334, it is contemplated that the fluid stream may be of any shape or configuration that allows resection according to the present embodiments. In particular, there are numerous advantages to both the columnar fluid stream configuration and the diverging fluid stream configuration, as will be described further below.

In a columnar fluid stream configuration 333, the device emits the fluid stream as a substantially focused rod-like fluid column that has a substantially zero divergence angle. In one embodiment, the columnar fluid stream is configured as a generally straight or non-diverging fluid stream. In such configuration, the device emits the fluid stream substantially as a cylinder or other non-diverging shape, thereby transmitting energy to the tissue over an area or spot size that is largely independent of the tissue distance from the fluid delivery element. Optionally, the fluid stream may be adjusted to converge, for example if the fluid delivery element comprises multiple nozzles or if the fluid contains bubbles, in order to focus the energy delivered to tissue.

Figure 6A:
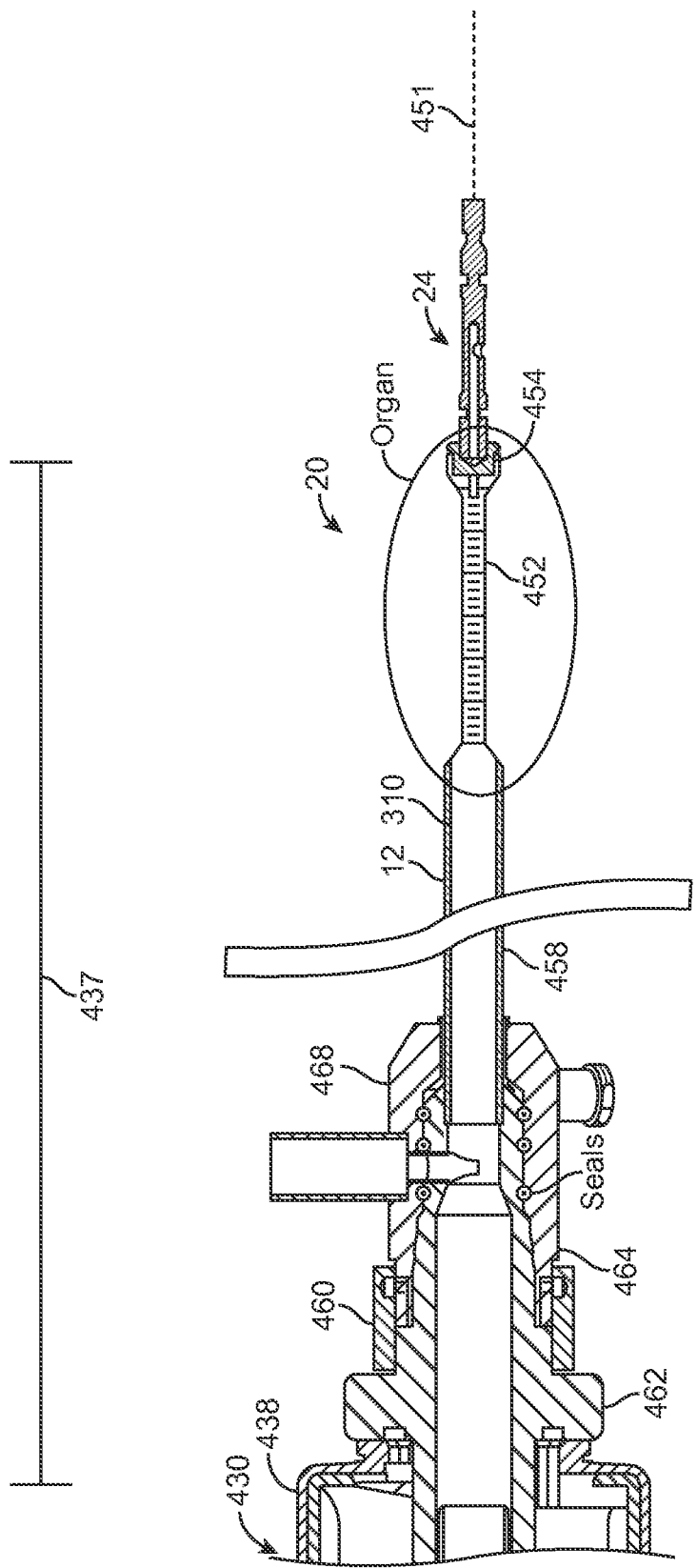
FIG. 6A shows a multipurpose sheath and manifold in accordance with embodiments.

FIG. 6A shows a multipurpose sheath and manifold in accordance with embodiments. A manifold 468 is configured to transmit a plurality of fluids to and from the working site. Manifold 468 is rigidly coupled, for example affixed, to the spine 452. A sheath 458 is located around spine 452 and can extend inward toward the manifold 468. The manifold 468 is coupled with a locking element 460 to support 438 in linkage 430. Manifold 468 can be decoupled from the linkage 430 and the support 438 so as to remove the linkage 430 and support 438 to permit additional components to be inserted into the working channel. For example, an endoscope can be inserted into the working channel to extend toward the working area of the organ, for example, the prostate. A structure 462 comprising a nose portion extends toward manifold 468. Structure 462 is shaped to engage manifold 468 and allow removal of structure 462, linkage 430 and support 438 when locking element 460 is disengaged. Manifold 468 comprises a structure 464 to engage in nose portion of structure 462. A plurality of seals are arranged on manifold 468 to allow removal of structure 462. When structure 462 has been removed an endoscope or other surgical tool can be inserted into the working space and advance toward the treatment site. For example an endoscope can be advanced toward the treatment site to be the treatment area. The manifold comprises a plurality of ports that are coupled to the treatment site to allow fluid to be transmitted and removed from the treatment site. For example when an endoscope has been placed at the treatment site. The locking element and manifold allow for removal of the linkage and treatment probes such that the manifold 468 remains coupled to sheath 458 and spine 452 within the patient.

In many embodiments treatment probes and carriers as described herein, for example tubular carriers, can be inserted and removed while the locking element 460 engages the linkage 430 and support 438. This configuration of the linkage, locking element and support allow probes to be rapidly and easily removed and reinserted to provide beneficial treatments.

The multipurpose sheath and manifold as described herein has the benefit of allowing the sheath, manifold, spine and anchor to remain attached to the patient while additional surgical tools are employed. The locking element interfaces with multiple instruments allowing for placement, visualization, and aquablation and aquabeam operations, without reintroduction or movement with respect to the tissue. Multiple sealed conduits allow for sheath ports to be used to transmit flow or pressure of varying fluids within or parallel to the working channel. The working channel may be used for visualization access to anatomy via existing rigid or flexible endoscope technology. The working channel has a large bore to accommodate many types of tools and allow for free flow of tissue and fluids. Alternate energy delivery devices may be used within the sheath or working channel as described herein.

In many embodiments the working channel is sized to allow a plurality of carriers within the working channel. For example, an endoscope carrier within the working channel and a treatment probe carrier as described herein within the working channel so as to allow visualization of the treatment site while the treatment probe performs aquablation and aqua beam operations as described herein.

Figure 6B:
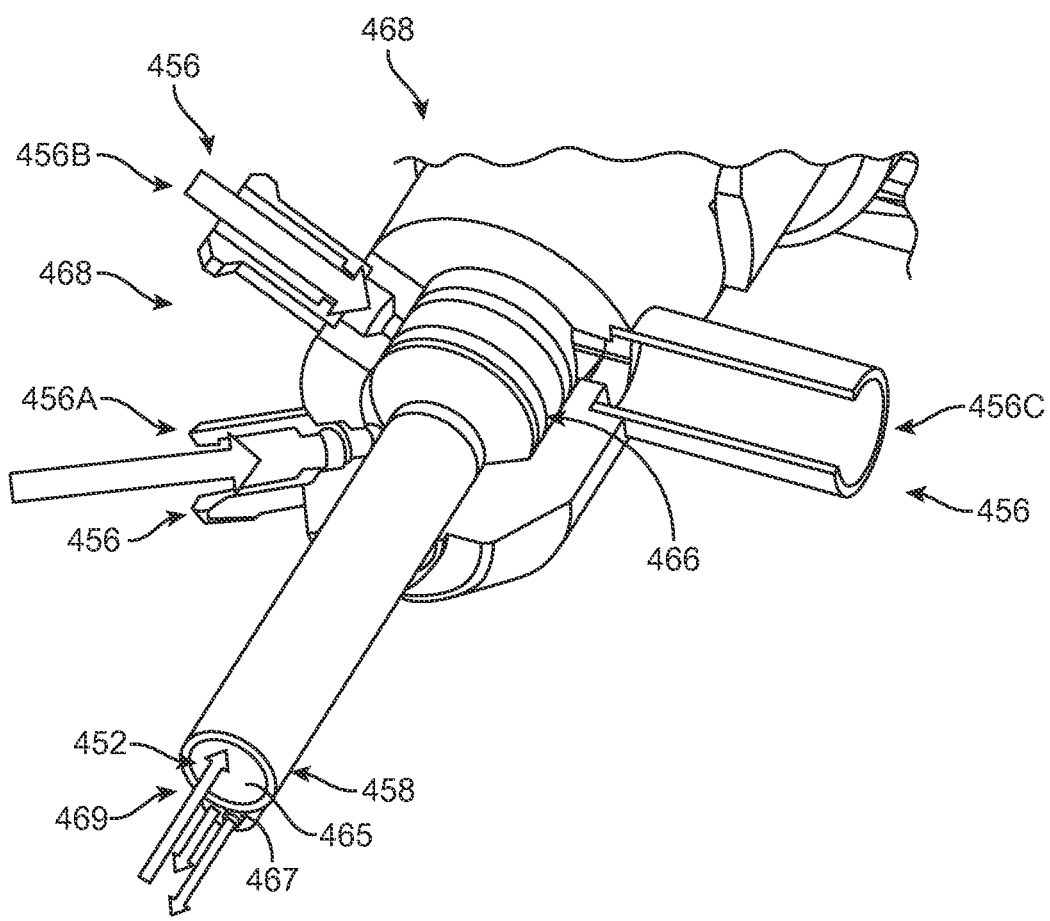
FIG. 6B shows manifold conduits of the manifold as in FIG. 6A configured for transmit and reception of multiple fluids while the manifold remains coupled to the patient in accordance with embodiments.

FIG. 6B shows manifold conduits of the manifold configured for transmitting and receiving multiple fluids while the manifold remains coupled to the patient. The manifold is coupled to a plurality of ports 456. The plurality of ports 456 may comprise an auxiliary fluid port 456A, a balloon pressure port 456B and a tissue removal port 456C. A sheath 458 extends circumferentially around spine 452. The spine 452 and sheath 458 can be rigidly coupled to the manifold portion and provide connections and channels coupled to the manifold portion. A channel 467, for example a tubular channel, is connected to port 456B to allow for inflation of the balloon. A channel 469 can be defined with sheath 458.

Channel 469 can be coupled to port 456A to provide an auxiliary fluid to the treatment site. Port 456C to allow removal of tissue can be coupled to the main working channel 465. The main working channel 465 can extend from port 456C to the treatment site. A plurality of seals 466 are arranged to separate the treatment ports and channels as described herein. The manifold 468 can be decoupled from the linkage 430 and support 438 and allow balloon inflation pressure to be applied through port 456B. An auxiliary fluid can be provided through port 456A, for example, so as to flush the working channel 465. This configuration of the manifold allows the spine 452 and anchor 24 to remain in place when other instruments have been inserted into the working channel.

The plurality of manifold conduits as described herein allow tissue collection to be routed through the large bore working channel 469 to reduce flow obstructions. Balloon pressure can be transmitted from a lure fitting to the distal tip of the anchor with small diameter tubing, for example, tubing defining channel 467. An auxiliary fluid is transmitted between the sheath and spine to the treatment area with channel 469.

Figure 6C:
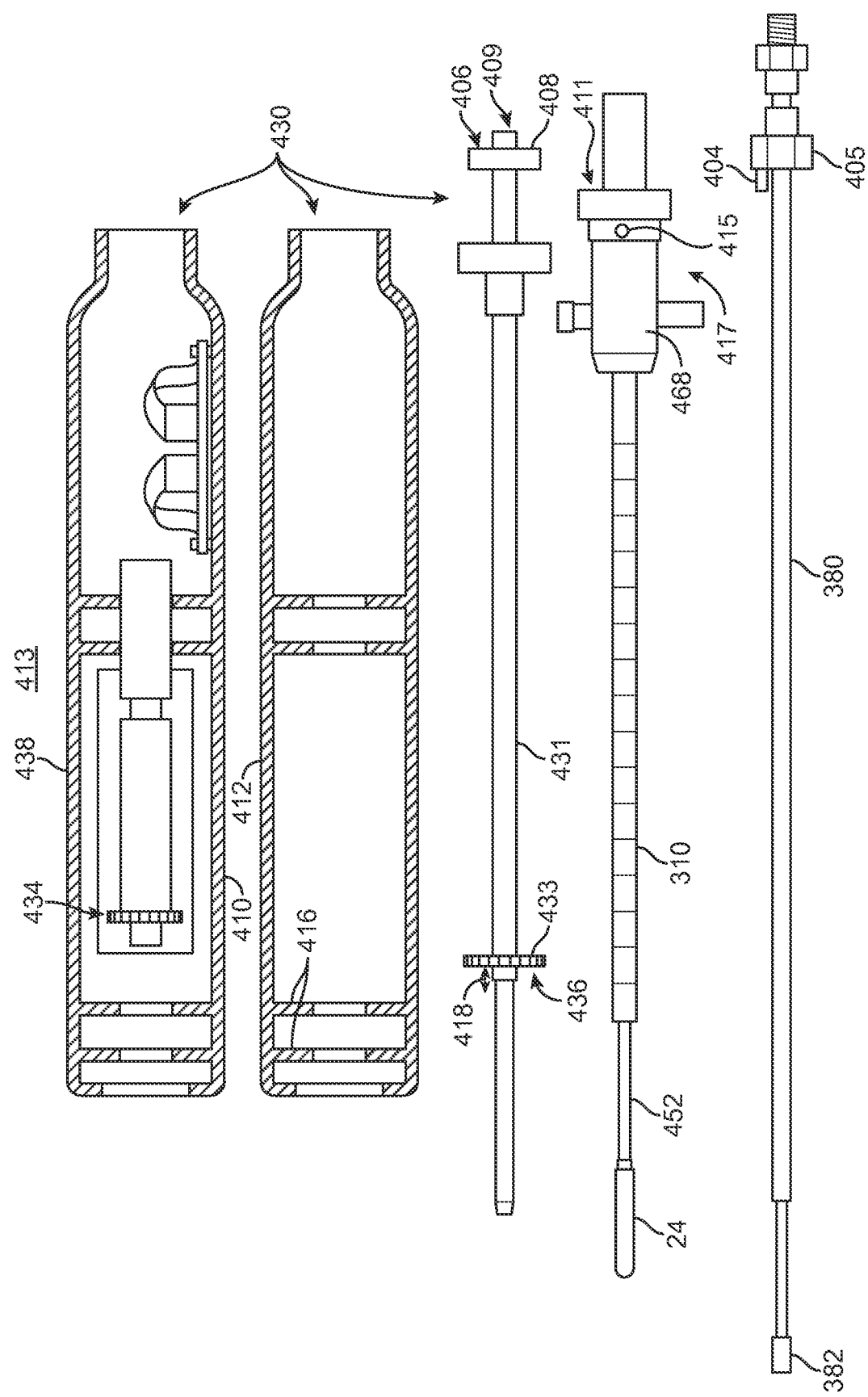
FIG. 6C shows components of treatment probe and linkage in accordance with embodiments.

FIG. 6C shows components of treatment probe and linkage disassembled prior to use. The linkage 430 comprises a casing 410 and a cover 412. The cover 412 can be placed on the lower portion of the casing 410. The cover and casing may comprise rigid materials to add stiffness. The casing and cover can be sized so as to comprise a handpiece containing the linkage 430. The linkage 430 comprises an elongate tubular structure comprising a gear 433 to engage another gear 434 of the linkage. The gear 434 can be positioned on a movable carriage 413. The elongate tubular structure may comprise second movable portion 436 of the linkage. The casing 410 may comprise the support 438 of the linkage. The gear 433 remains connected to the elongate tubular structure 431 when the linkage is disassembled. The movables portion of the linkage 430 may comprise gear 433, gear 434 and movable carriage 413 so as to advance the elongate structure 431 distally when connected to the second movable portion 436 as shown with arrows 418. The cover 412 comprises flanges 416. When the cover is placed on the casing, the elongate structure can be locked into position 431 on the linkage.

The elongate element 310 comprises a spine 452 as described herein and is shown covered with a sheath 458. The sheath 458 comprises a channel to receive the elongate element 310. The elongate element 310 comprises the working channel and can inserted into the sheath 458 such that the elongate element is covered with sheath 458. The sheath 458 and elongate element 310 are shown connected to manifold 468 as described herein.

The sheath 458 can be inserted into the patient prior to insertion of elongate element 310. In many embodiments, sheath 458 is coupled to manifold 468 when inserted into the patient.

The elongate element 310 is configured to slide into the sheath 458 such that the elongate element 310 and sheath comprise a locked configuration. The elongate element 310 comprises structure 411 configured to engage the housing 410 of the linkage, such that the elongate element 310 and housing 410 remain substantially fixed when the elongate structure 431 moves as described herein.

In many embodiments, casing 410 comprises support 438. The support 438 may comprise a substantially non-moving portion of the linkage 430 as described herein. The linkage 430 may comprise moving carriage 433 to move the carrier 382 when the casing 410 comprising support 438 remains locked to the arm and substantially non-moving as described herein.

In many embodiments, the structure 411 of the elongate element 310 comprises locking structure to form a locked joint with the casing 410 and cover 412.

In many embodiments, manifold 468 is connected to the sheath 458 and can be affixed to the sheath to inset the sheath 458 into the patient and inflate the balloon anchor 24 with the manifold 468 as described herein. The elongate element 310 comprising spine 452 may then be inserted into sheath 458. The manifold 468 and structure 411 comprises locking structures 417 to lock the manifold to the elongate element 310 when the elongate element 310 has been inserted into the manifold 468 and sheath 458. A release 415 can be pressed by the user to unlock the manifold 468 from the elongate element 310.

The elongate tubular structure 431 of the linkage 430 comprises structures to receive the carrier tube 380. An opening 409 of the elongate tubular structure 431 is sized to receive the carrier tube 380. A connection structure 408 is shown on the proximal end of the linkage, and comprises a locking structure 406 to receive a protrusion 404 of the connection structure 405 of carrier tube 308.

FIG. 6D1 shows rapid exchange of a carrier tube 380 when the linkage 430 is coupled to the elongate element 310 anchored to a target location of an organ. The elongate element 410 can be inserted or removed from the linkage by the user. The elongate element 380 can be advanced into opening 409 near connection structure 405 of the elongate tubular structure 431.

The imaging probe 460 can be mounted on a second linkage and configured to move with the nozzle of carrier 382, so as to image interaction of the energy stream from carrier 382 when tissue is treated. The images of the treatment may comprise axial images and sagittal images from the imaging probe 460. The linkage can be coupled to the controller or processor (or both) as described herein to move the imaging probe 460 synchronously along the axis with the carrier 382 and nozzle of the carrier, for example. The imaging probe 460 may comprise a trans-rectal ultrasound probe and the carrier 482 may comprise a component of the treatment probe 450 as described herein.

FIG. 6D2 shows alignment of the distal tip of the carrier 382 with the opening 409 of proximal end of the elongate tubular structure 431 to insert the carrier tube 380 as in FIG. 6D1.

FIG. 6D3 shows the carrier advanced toward a locking structure 406 on the proximal end of the linkage as in FIG. 6D1. The locking structure 406 is sized to receive protrusion 404 so as to form a locked joint 402.

FIG. 6D4 shows the carrier tube 380 locked to the linkage 430 as in FIGS. 6D1 and 6D2. The protrusion 404 has been inserted into an opening of locking structure 406 so as to form the locked joint. The joint can be unlocked by user manipulation.

Figure 6E:
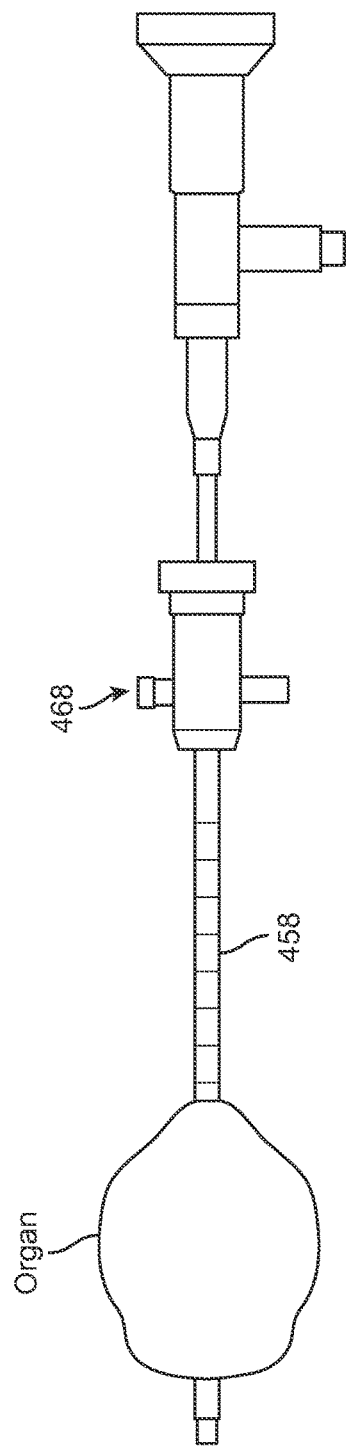
FIG. 6E shows a cystoscope inserted at least partially into an elongate element for advancement toward a bladder neck to view tissue of an organ such as the prostate, in accordance with embodiments.

FIG. 6E shows a cystoscope inserted at least partially into a sheath 458 for advancement toward an anchoring location of an organ. The anchoring location may comprise a bladder neck to view tissue of an organ such as the prostate. The sheath 458 as described herein can be advanced to a target location with visualization from the cystoscope placed within the working channel of the elongate element 310. When positioned, the anchor 24 such as a balloon can be inflated with a port of manifold 468 coupled to the sheath as described herein.

There are at least two forms of visualization possible with the embodiments as described herein. 1) The cystoscope is locked within the sheath 458. The purpose can be to view the prostate and then eventually leave the sheath as a safe channel to guide the elongate element 310 comprising spine 452 into the patient, in many embodiments without having direct visualization. The distal end of the sheath lines up near bladder neck. 2) Once the elongate element 310 is locked into the sheath 458, ureteroscope can be used to view the patient. The ureteroscope can be inserted inside the same channel that carrier 380 goes into, for example shared channel.

FIG. 6F shows advancement of an elongate element 310 into a sheath 458. The manifold 468 on the proximal end of the sheath 458 may comprise a locking structure to receive a locking structure on the proximal end of elongate element 310. The elongate element 310 can be advanced into sheath 458 such that the locking elements on the sheath 458 and elongate element 310 engage.

Figure 6G:
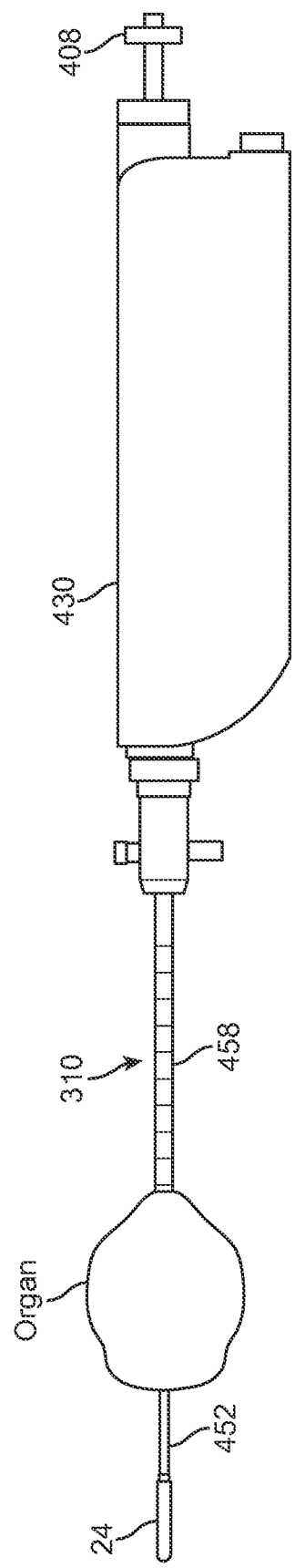
FIG. 6G shows a linkage coupled to an elongate element comprising a spine in accordance with embodiments.

FIG. 6G shows a linkage 430 coupled to an elongate element 310 comprising a spine 452. The linkage is configured to receive carrier 382 and carrier tube 380 as described herein.

Figure 6H:
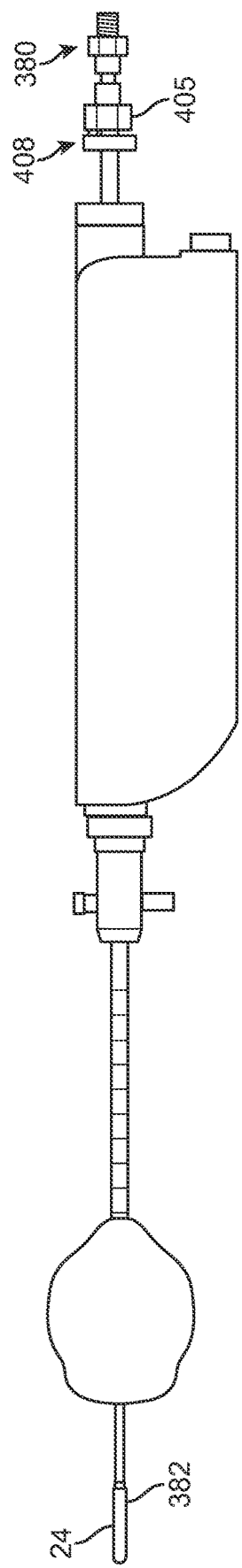
FIG. 6H shows a carrier tube and carrier inserted into the linkage tube in accordance with embodiments.

FIG. 6H shows a carrier tube and carrier inserted into the linkage tube in a locked configuration as described herein.

FIGS. 6A to 6H show a method of treating a patient in accordance with embodiments, and each of these figures shows one or more optional steps of the method.

Figure 7:
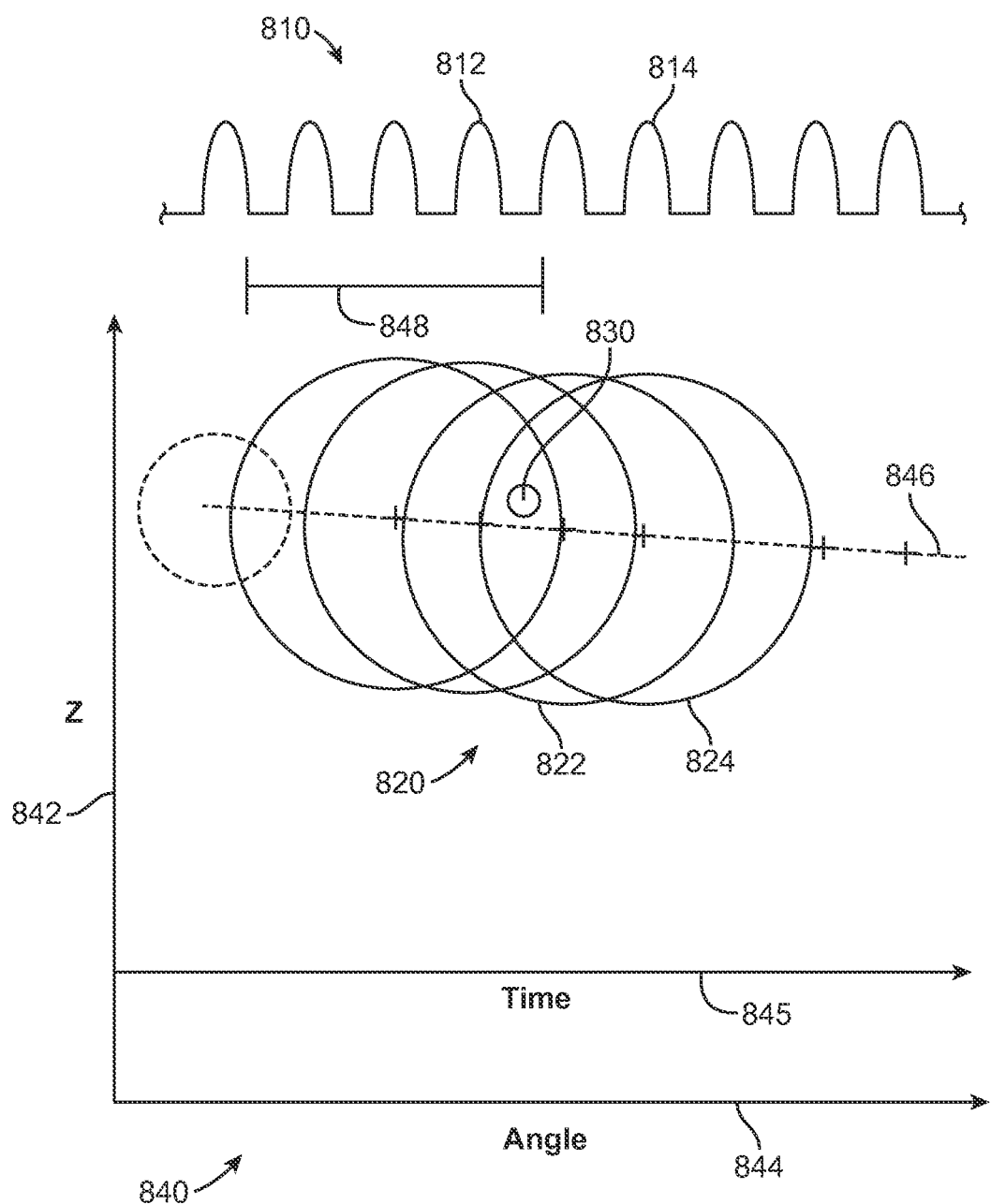
FIG. 7 shows scan patterns of the fluid stream, in accordance with embodiments.

FIG. 7 shows scan patterns of the fluid stream as described herein. The fluid stream may comprise a pulsed or continuous fluid stream. The scan pattern can be based on critical pressures as described herein so as to remove a first tissue and inhibit removal of a second tissue. In many embodiments, the fluid stream comprises a plurality of pulses 810 from a pump such as a piston pump, and the pulses comprise a frequency and duty cycle. In many embodiments, the duty cycle correspond to no more than about 50%. The plurality of pulses 810 comprises a first pulse 812 and a second pulse 814. The fluid flame may comprise an approximate cross sectional size at the location of tissue being scanned. Based on the teachings described herein, a person of ordinary skill in the art will recognize that the fluid flame comprises a maximum cross sectional width at about ½ the length of the fluid flame. At the location where the fluid flame impinges upon tissue, the fluid flame comprises a cross sectional size 848.

The scanning pattern of the fluid stream comprising the fluid flame are along a Z-axis and angle 844. The angle 844 may correspond to time 845, for example when the angular sweep rate remains substantially constant. The fluid flame is scanned along a scan path 846. The scan path 846 may correspond to the velocity of the carrier 382 along the Z-axis and the rotation of the carrier 382 around the Z-axis, for example.

The pulses can be spaced apart such that a plurality of sequential pulses strike a location 830 of tissue. The plurality of sequential pulses can be effective in removing a first type of tissue when removal of a second type of tissue is inhibited.

Alternatively or in combination with the critical pressures as described herein, work in relation to embodiments suggests that the rate of removal can be related to a relaxation time of a targeted tissue. The fluid flame can be configured to dwell on a point 830 of tissue for a duration longer than the relaxation time of the tissue, such that the tissue can be deformed beyond a threshold and removed.

In many embodiments, the plurality of pulses 820 impinge upon the tissue location 830 with a duration between pulses that is less than a tissue relaxation time of elastic deformation of the tissue so as to remove the tissue. In many embodiments, a first tissue to be removed comprises a first relaxation time greater than the time between pulses, and the second tissue for which removal is to be inhibited comprises a second tissue relaxation time less than the time between pulses, so as to inhibit removal of the second tissue.

As the tissue is removed toward the final desired treatment profile, the size of the fluid flame may decrease substantially near the distal tip of the flame, such that the size of the pulsed fluid flame impinging upon the resected profile is decreased substantially tissue removal decreased substantially.

Based on the teachings described herein, a person of ordinary skill in the art can determine the scanning movement of the carrier 382 and nozzle to resect tissue to a target profile with the fluid flame as described herein.

Figure 8:
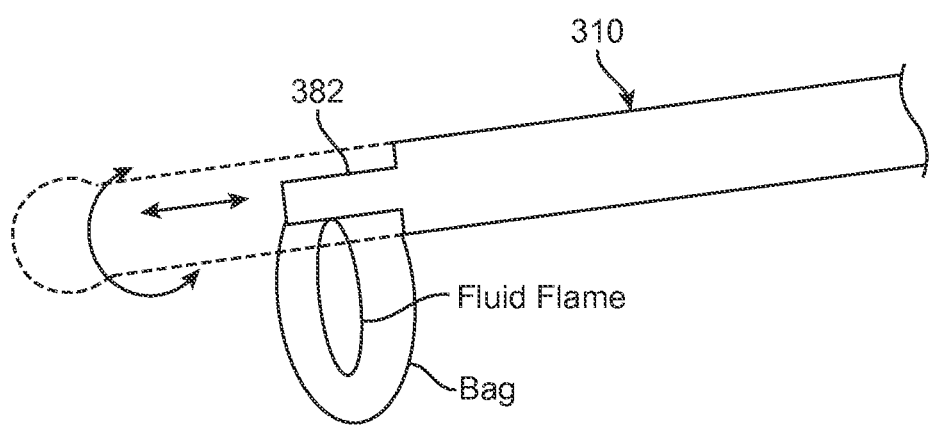
FIG. 8 shows a bag over a fluid stream comprising a water hammer in accordance with embodiments.

FIG. 8 shows a bag over a fluid stream. The fluid stream may comprise the columnar stream or divergent stream as described herein. In many embodiments the bag is placed over a fluid stream comprising a pulsed stream so as to comprise a water hammer. The bag can be made of one or more of many materials and may comprise an elastomer, for example. The interior of the bag can be coupled to the carrier 382, and the exterior of the bag can be coupled to the working channel to remove material. The bag has the advantage of protecting the tissue from the high fluid flow rate and can provide more even pressure. The fragmented tissue can be collect through passive or active means, for example through an outer collection tube or the working channel.

Figure 9A:
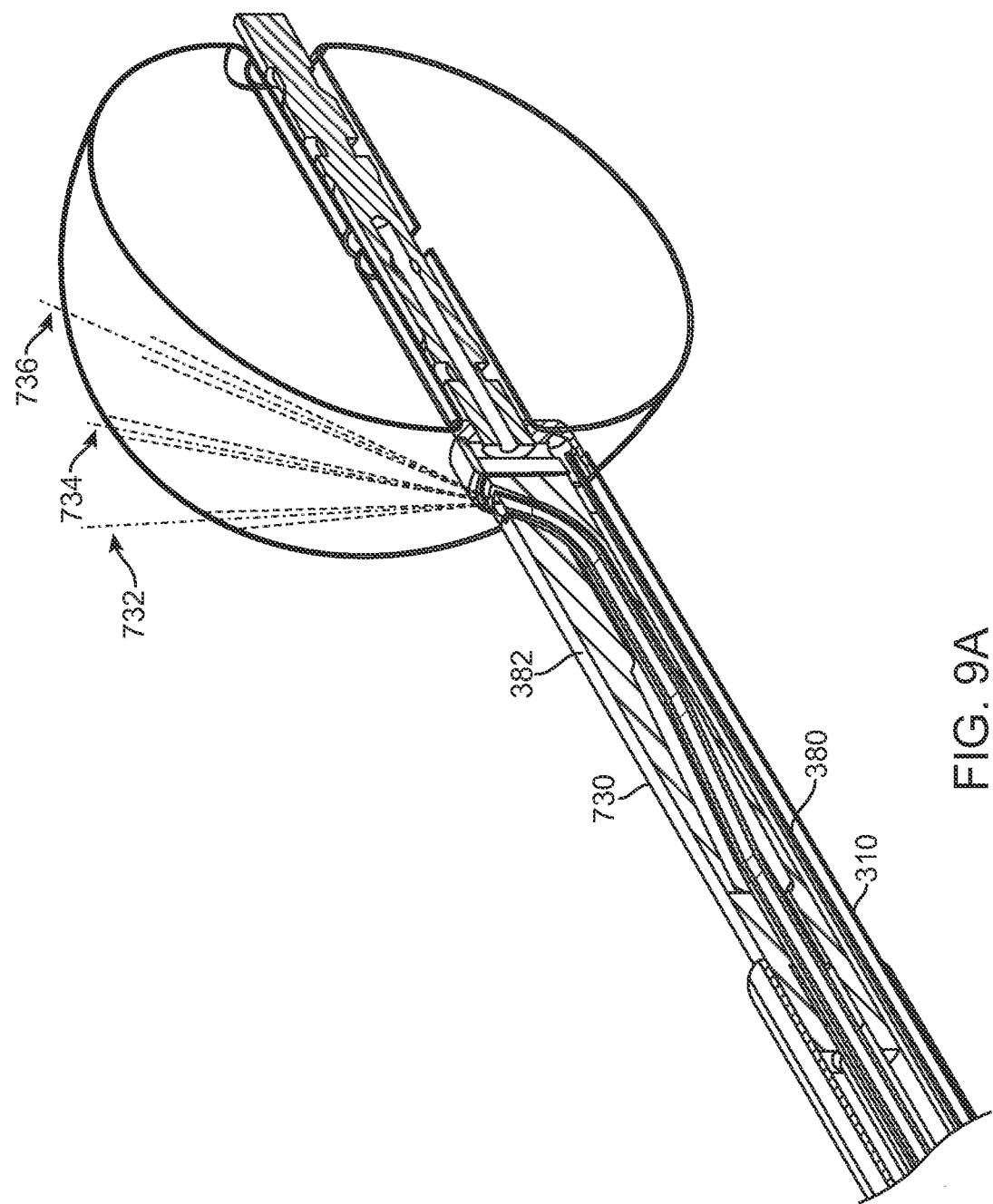
FIGS. 9A and 9B show variation of jet angle in accordance with embodiments.
Figure 9B:
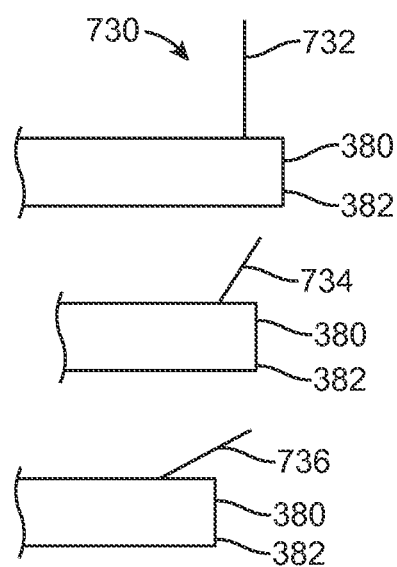

FIGS. 9A and 9B show variation of jet angle in accordance with embodiments. The fluid jet angle and the laser beam can be fixed at different angles to achieve cutting or coagulation. The one or more of cutting or coagulation can be directed to a single location or multiple locations, for example. Angling can assist in targeting tissue near an expandable anchor such as a balloon or reduce risk of incidental contact with unintended tissue. The jet angle can be varied in one or more of many ways. For example, a plurality of carriers 730 can be provided, and each of the carriers may comprise carrier 382 having structures and components for treatment as described herein. Each of the plurality of carriers 730 can provide a different fluid stream angle. For example, a first carrier can provide a first angle 732. A second carrier can provide a second jet along the second angle 734 and a third carrier can provide a third angle 736 as shown. The plurality of probes may comprise a set of probes, for example, three or more probes in which each probe is configured to direct one or more of the jet angle or the laser beam at an angle. For example, first angle 732 can extend substantially perpendicular to the elongate axis and third angle 736 can be directed toward a distal end of the probe in order to resect medial tissue, for example tissue of the prostate.

In many embodiments, a plurality of probes can be provided in which one or more jets exits the device axially to target tissue immediately distal of the device.

Figure 10:
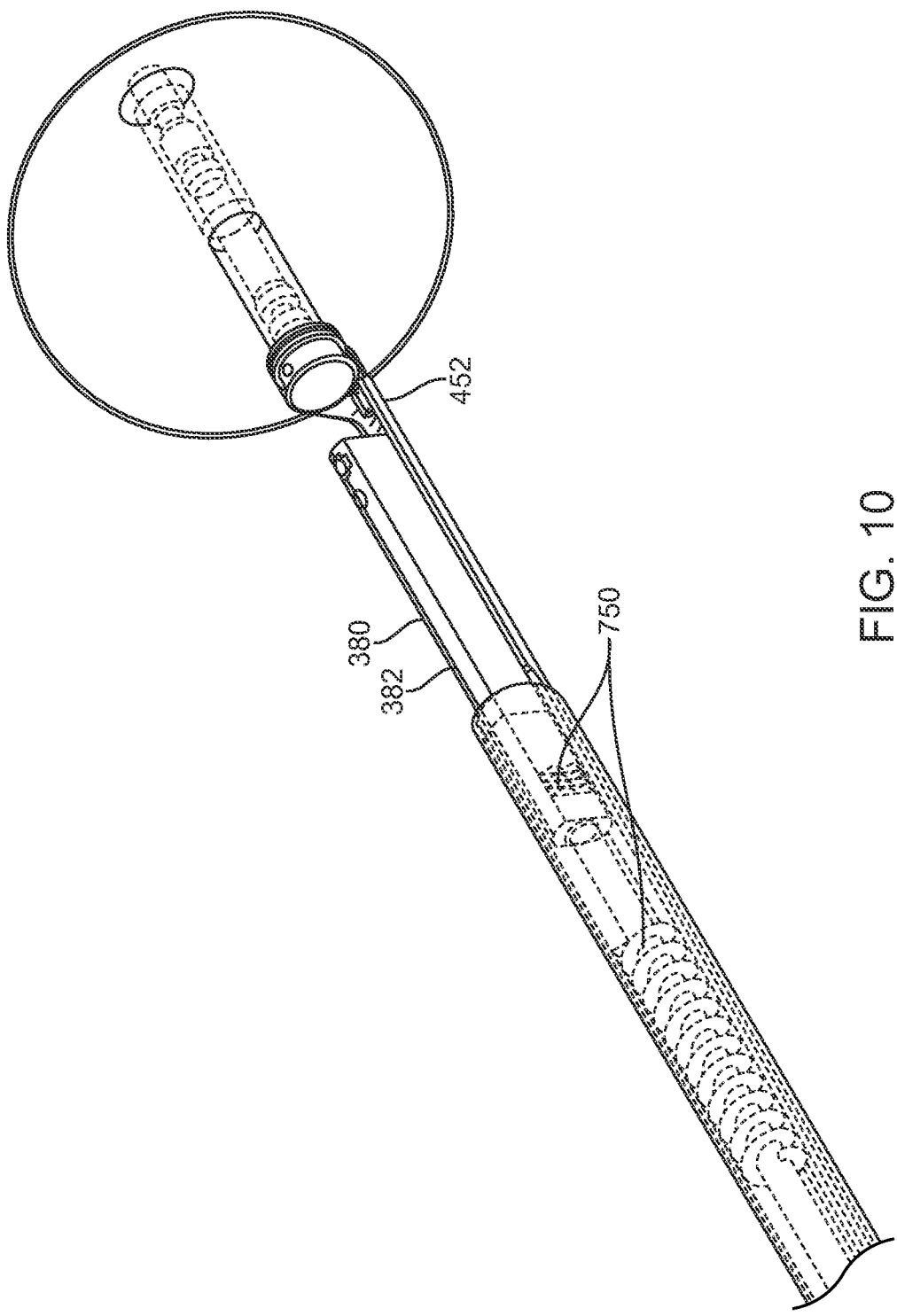
FIG. 10 shows morcellation in accordance with embodiments.

FIG. 10 shows morcellation in accordance with embodiments. In many embodiments, morcellation can be achieved concurrently with ablation with structural features such as blades on the probe or spine for example. If integrated to the probe, morcellation can be automatically driven by the movement of the probe. Vacuum suction can be used along-side or independently with physical morcellation to increase collection flow. The combination of physical morcellation for example with an auger structure and vacuum can be utilized to regulate intraorgan pressure.

Carrier 382 can extend to a distal end portion having one or more jets as described herein. Morcellating features can be provided proximately with respect to the jets and the morcellating features may be contained within the working channel, for example, with an auger shaped structure to remove tissue.

Figure 11A:
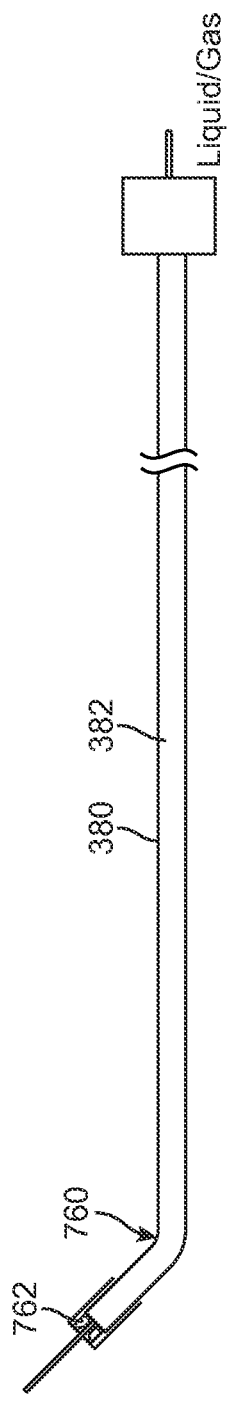
FIGS. 11A to 11C shows single tube designs in accordance with embodiments.
Figure 11B:
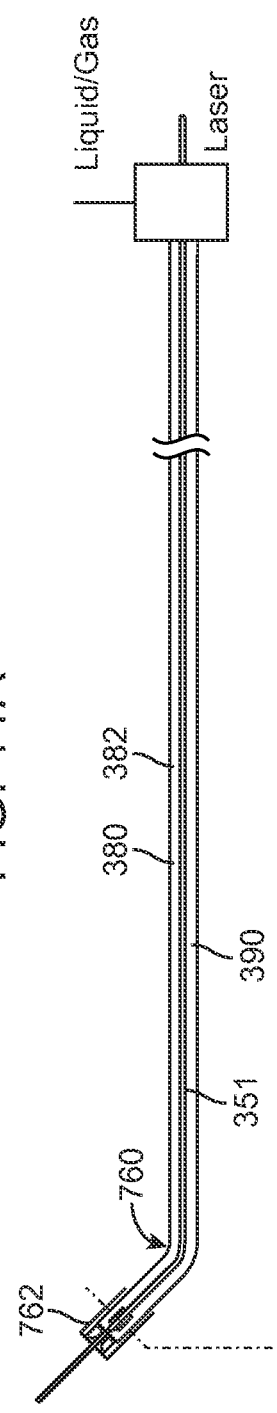
Figure 11C:
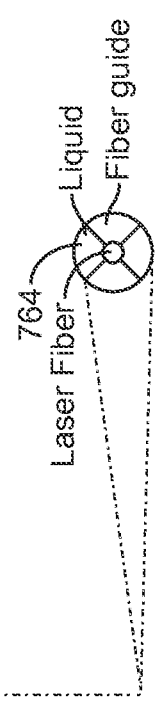

FIG. 11A shows a single tube design in accordance with embodiments. The single tube design may comprise a fluid delivery element such as an orifice jewel 762. A variable bend 760 allows a radius to bend, for example, when the carrier 382 is advanced within the working channels. A fluid is coupled to the orifice on the end of the carrier 382. The fluid may comprise liquid or gas and the orifice on the distal end can be configured in one or more of many ways as described herein. FIGS. 11B and 11C show a single tube design in accordance with embodiments. A fluid such as a liquid or gas can be coupled with a laser as described herein. The laser can emit electromagnetic energy transmitted along an energy conduit 351 such as an optical fiber as described herein. A variable bend 760 can be provided near the fluid delivery element such as an orifice jewel 762 on the distal end. The optical fiber can be aligned with structures as shown in FIG. 11C. For example, a fiber guide can be used to locate the optical fiber coaxially with the orifice of the fluid jet.

The single tube design in accordance with the embodiments of FIGS. 11A, 11B, and 11C can provide many advantages. For example, package size and complexity can be greatly reduced when utilizing a single tube design. Internal laminar flow characteristics can be improved with a single tube design as the fluid path can be more continuous than with other designs, for example. The orifice jewel can be swaged in place or a small cover can be laser welded to retain the jewel. Optical fiber integration can be achieved through the use of an internal fiber alignment structure. The bend angle and radius can be varied so as to allow for alternate tissue targeting or for manufacturing. Multiple jets can be employed to balance jet reaction courses and cut more than one location concurrently. For example, opposing jets can be used. An additional jet may be added to power rotational motion of the catheter for example.

The small package size can allow the implementation to take the form of a small catheter. This can allow for use with prior commercially available rigid and flexible introducers and scopes. The distal tip shapes can be preformed with a given bend angle to access a tissue volume.

Figure 13:
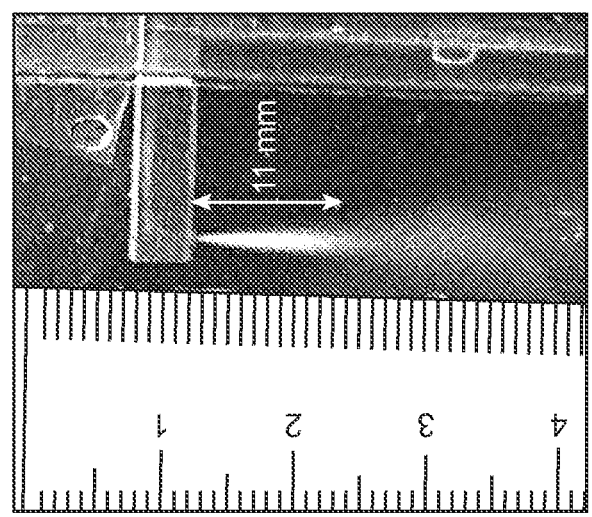
FIG. 13 shows the visible entrainment region at a first size as is shown in FIG. 12.
Figure 12:
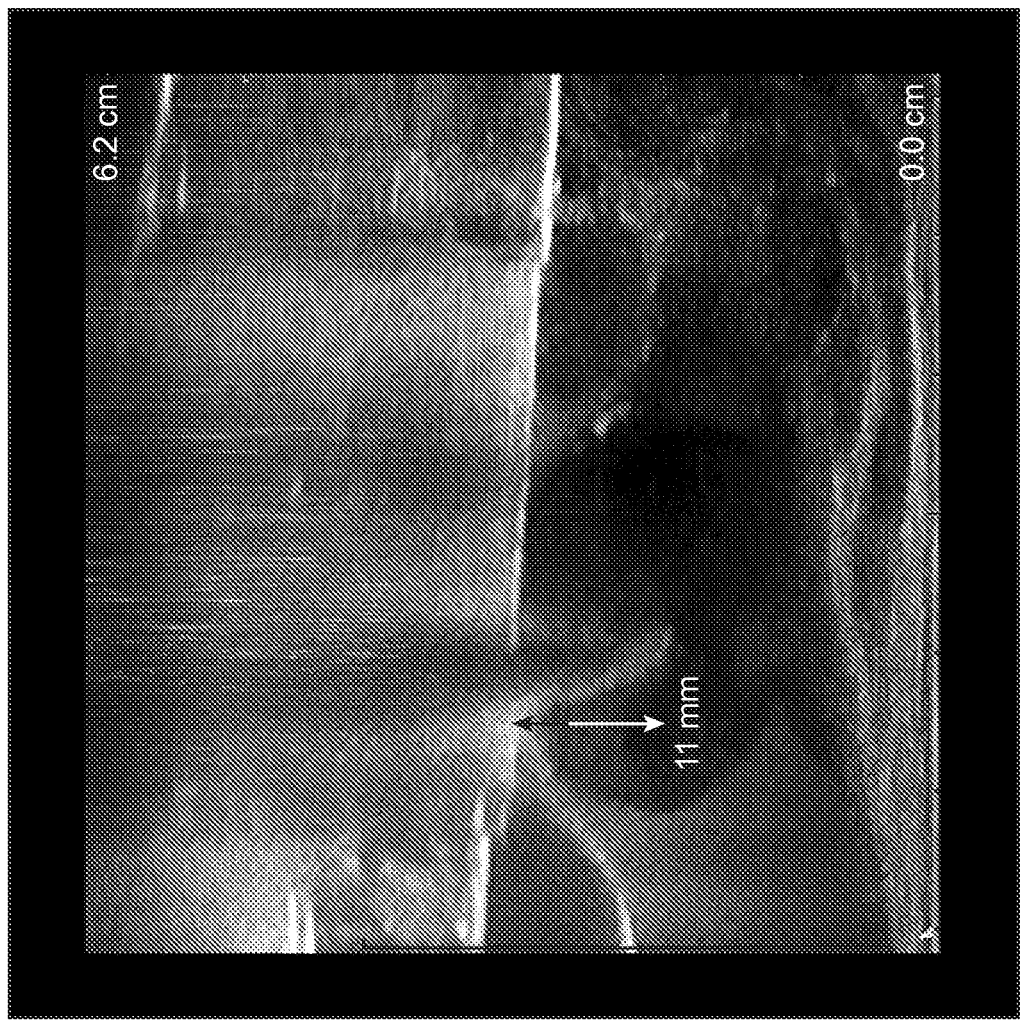
FIG. 12 shows tissue resection and depth control in accordance with embodiments.

FIG. 12 shows tissue resection and depth control in accordance with embodiments. A live patient ultrasound image is shown. FIG. 13 shows a visible fluid flame in saline. The visible fluid flame in saline corresponds to the entrainment region of the jet as described herein. The visibility of the fluid flame of the entrainment region is provided with cavitation of small bubbles that can produce light scattering or acoustic scattering, so as to make the fluid flame of the entrainment region visible with imaging by ultrasound or optical imaging, for example. The benefit of the visible entrainment region can be for a physician to visualize the distance of the treatment and to compare this distance with ultrasound. FIG. 13 shows the visible entrainment region at 11 millimeters, the same size as is shown in FIG. 12. The substantial similarity of the distance of the entrainment region corresponds to the distance of tissue resection and removal. This experimental result showing the visualization of the entrainment region can provide for a safer treatment. Merely by way of example, the flow parameters used with the images shown in FIGS. 12 and 13 comprise a flow rate of approximately 130 milliliters per minute and a nozzle back pressure of approximately 2700 psi. The configuration of the nozzle on the carrier comprise a first liquid emitted with a divergent stream as described herein into a second fluid so as to provide the divergent stream. The second fluid comprises a liquid.

A physician when treating a patient, can use a live patient ultrasounds, for example, transrectal ultrasound (hereinafter "TRUS") as described herein. The physician can do the ultrasound in the entrainment region from the probe tip. This can be used to determine the appropriate parameters to treat the patient. For example, the physician can adjust the pressure so as to limit the depth of penetration of the probe tip such that the probe tip does not release energy to cause cutting outside of the organ, for example, beyond the sack of the organ such as the sack of the prostate. The image of FIG. 12 shows on the left hand side of the image a structure corresponding to an expandable balloon and the arrows show the 11 millimeter dimension. FIG. 13 is an optical image showing a similar distance of the entrainment region. The sweeping motion of the stream shown in FIG. 12 can be used to adjust the treatment to be contained within the prostate.

Figure 14:
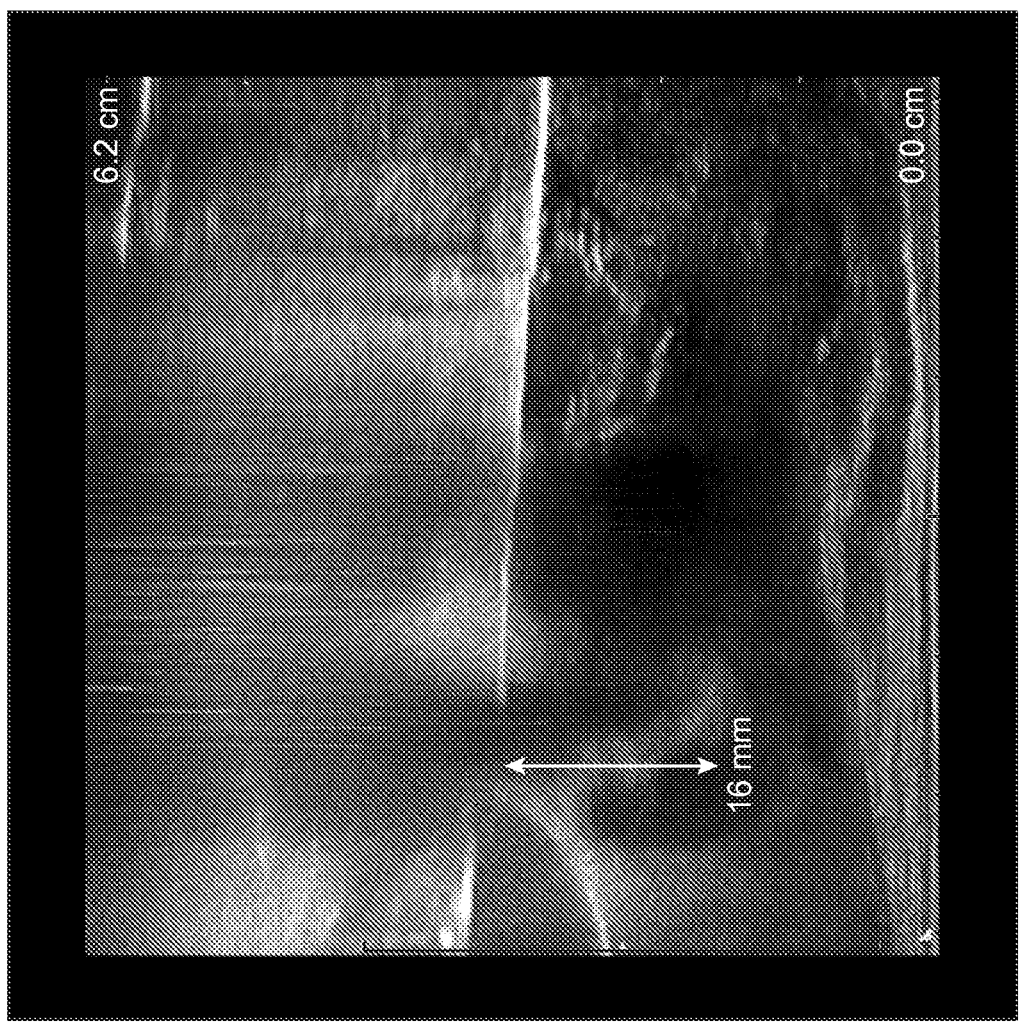
FIG. 14 shows tissue resection depth control in accordance with embodiments.

FIG. 14 shows tissue resection depth control in accordance with embodiments. Live patient ultrasound from the patient is shown in FIG. 14 similar to FIG. 13, but with increased back stream pressure to the nozzle.

Figure 15:
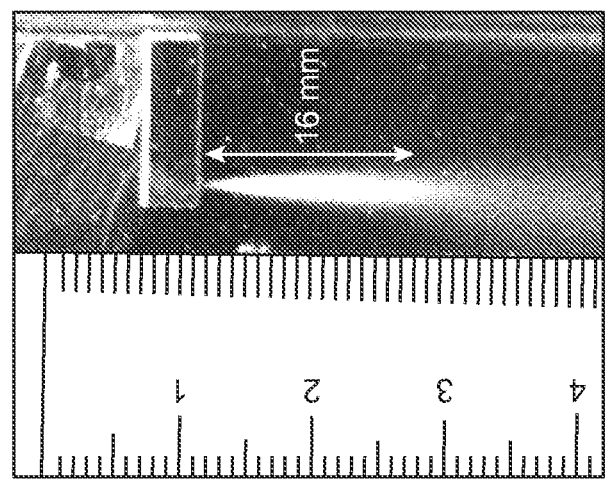
FIG. 15 shows an optical image of the entrainment region "flame" in saline as shown in FIG. 14 with a different pressure than is shown in FIGS. 12 and 13, in accordance with embodiments.

FIG. 15 shows an optical image of the fluid flame in saline showing the entrainment region with a different pressure. The pressure flow parameters for FIGS. 14 and 15 comprise an approximate flow rate of 205 milliliters per minute and the nozzle back pressure of approximately 5760 psi. The corresponding tissue resection depth is approximately 16 millimeters. The live patient ultrasound image shows an entrainment region of 16 millimeters similar to the entrainment region seen optically. The sweeping motion of the probe and the fluid stream emitted from the probe as seen on the left hand side of the image can be used to set the flow parameters and pressure so as to treat the patient safely with ultrasound images of the entrainment region.

A person of ordinary skill in the art can use the one or more of the nozzle pressure, cut depth and flow rates to resect tissue to a predefined profile and volume as described herein.

While preferred embodiments of the present disclosure have been shown and described herein, it will be obvious to those skilled in the art that such embodiments are provided by way of example only. Numerous variations, changes, and substitutions will be apparent to those skilled in the art without departing from the scope of the present disclosure. It should be understood that various alternatives to the embodiments of the present disclosure described herein may be employed without departing from the scope of the present invention. Therefore, the scope of the present invention shall be defined solely by the scope of the appended claims and the equivalents thereof.

What is claimed is:

1. A method of enucleating at least a portion of a prostate, the prostate comprising a capsule and an inner layer of prostate tissue, the method comprising:
   advancing a probe at least partially into a patient;
   resecting a first location and a second location with a
      visible water jet provided at a first amount of energy;

adjusting the visible water jet from the first amount of energy to a second amount of energy based on a visualization of the visible water jet while treating tissue; and separately enucleating a plurality of lobes of the prostate by separating the capsule from the inner layer of prostate tissue with the visible water jet provided at the second amount of energy and having a length, measured from a water jet orifice to a tip of the visible water jet, within a range from 1 mm to 5 mm.

2. The method of claim 1, wherein the probe is advanced into the patient with one or more of open surgical access, percutaneous access or urethral access.

3. The method of claim 1, wherein the first location is situated near a bladder neck of a urethra and the second location is situated near a verumontanum and toward the bladder neck from the verumontanum.

4. The method of claim 1, wherein the resecting comprises a plurality of resections extending between the first location and the second location and wherein the plurality of resections extend from a urethra to the capsule.

5. The method of claim 1, wherein the second amount of energy is adjusted to separate the capsule from the inner layer of prostate tissue and inhibit resection of the capsule and blood vessels.

6. The method of claim 1, wherein the visible water jet comprises a divergent stream.

7. The method of claim 1, wherein an energy of the visible water jet is adjusted based on an image of an entrainment region of the visible water jet when the probe has been inserted at least partially into the patient.

8. The method of claim 1, wherein the probe is advanced into a natural opening of a urethra to access the urethra and wherein the urethra is resected at the first location and the second location with the probe with the visible water jet extending at an first angle to a side of the probe to resect the urethra and wherein the capsule is separated from the inner layer with the visible water jet extending from an end of the probe at a second angle, different than the first-angle.

9. The method of claim 1, further comprising morcellating at least one of the plurality of enucleated lobes of the prostate, wherein the morcellating occurs after separately enucleating at least one of the plurality of lobes of the prostate.

10. The method of claim 1, wherein the enucleating occurs at a distance beyond a distal tip of an entrainment region of the visible water jet.

* * * * *